(12) United States Patent
Chen et al.

(10) Patent No.: US 12,076,173 B2
(45) Date of Patent: Sep. 3, 2024

(54) SYSTEM AND METHOD FOR CONTROLLING ERRORS IN COMPUTED TOMOGRAPHY NUMBER

(71) Applicant: WISCONSIN ALUMNI RESEARCH FOUNDATION, Madison, WI (US)

(72) Inventors: Guang-Hong Chen, Madison, WI (US); Ke Li, Middleton, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 387 days.

(21) Appl. No.: 17/512,236

(22) Filed: Oct. 27, 2021

(65) Prior Publication Data

US 2023/0132514 A1 May 4, 2023

(51) Int. Cl.
| A61B 6/42 | (2024.01) |
| A61B 6/00 | (2024.01) |
| A61B 6/03 | (2006.01) |
| G06T 11/00 | (2006.01) |

(52) U.S. Cl.
CPC ............ *A61B 6/4241* (2013.01); *A61B 6/032* (2013.01); *A61B 6/5205* (2013.01); *G06T 11/005* (2013.01); *G06T 2211/40* (2013.01)

(58) Field of Classification Search
CPC ..... A61B 6/4241; A61B 6/032; A61B 6/5205; G06T 11/005; G06T 2211/40
See application file for complete search history.

(56) References Cited

U.S. PATENT DOCUMENTS

| 6,256,367 | B1 | 7/2001 | Vartanian |
| 11,967,410 | B2* | 4/2024 | Blakely ................. G01N 35/00 |
| 2006/0067467 | A1 | 3/2006 | Clinthorne et al. |
| 2012/0070050 | A1* | 3/2012 | Panin .................... G06T 11/005 382/131 |
| 2015/0238161 | A1* | 8/2015 | Petschke ................ A61B 6/587 378/19 |
| 2016/0095561 | A1* | 4/2016 | Tamura .................. A61B 6/032 378/62 |
| 2016/0242720 | A1* | 8/2016 | Ida ......................... A61B 6/032 |
| 2017/0265833 | A1 | 9/2017 | Danielsson et al. |
| 2018/0322617 | A1* | 11/2018 | Carmi .................... G06T 11/003 |
| 2018/0368781 | A1* | 12/2018 | De Man ................. A61B 5/055 |
| 2021/0007694 | A1 | 1/2021 | Hein et al. |

(Continued)

FOREIGN PATENT DOCUMENTS

WO 2023076504 5/2023

OTHER PUBLICATIONS

J. P. Cruz-Bastida, R. Zhang, D. Gomez-Cardona, J. Hayes, K. Li, and G.-H. Chen, "Impact of noise reduction schemes on quantitative accuracy of CT numbers," Med. Phys., vol. 46, No. 7, pp. 3013-3024, 2019.

(Continued)

*Primary Examiner* — Utpal D Shah
(74) *Attorney, Agent, or Firm* — Quarles & Brady, LLP

(57) ABSTRACT

A system and method for creating computed tomography (CT) images includes acquiring or accessing sinogram data and determining a photon count for the sinogram data. The method includes generating unbiased sinogram data from the sinogram data using an unbiased estimator and the photon count and reconstructing a CT image from the unbiased sinogram data.

18 Claims, 11 Drawing Sheets

(3 of 11 Drawing Sheet(s) Filed in Color)

(56) References Cited

U.S. PATENT DOCUMENTS

2023/0309937 A1\* 10/2023 Sossin ................ G06V 10/774 378/5
2023/0326100 A1\* 10/2023 Eguizabal ............ A61B 6/5211 382/156

OTHER PUBLICATIONS

J. P. Cruz-Bastida, R. Zhang, D. Gomez-Cardona, and G.-H. Chen, "Quantitative low-dose CT: potential value of low signal correction methods," Proc. SPIE, vol. 10948, pp. 762-767, 2019.

J. Fessler, "Hybrid poisson/polynomial objective functions for tomographic image reconstruction from transmission scans," IEEE Transactions on Image Processing, vol. 4, No. 10, pp. 1439-1450, 1995.

J. Hayes, R. Zhang, C. Zhang, D. Gomez-Cardona, and G.-H. Chen, "Unbiased statistical image reconstruction in low-dose CT," Proc. SPIE, vol. 10948, pp. 1246-1251, 2019.

International Search Report and Written Opinion for corresponding PCT Application No. PCT/US2022/048072, mailed Feb. 1, 2023, 9 pages.

G. Vegas-Sanchez-Ferrero, M. J. Ledesma-Carbayo, G. R. Washko, and' R. S. J. Estepar, "Autocalibration method for non-stationary CT bias' correction," Medical Image Analysis, vol. 44, pp. 115-125, 2018.

R. Zhang, J. P. Cruz-Bastida, D. Gomez-Cardona, J. W. Hayes, K. Li, and G.-H. Chen, "Quantitative accuracy of CT numbers: Theoretical analyses and experimental studies," Med. Phys., vol. 45, No. 10, pp. 4519-4528, 2018.

\* cited by examiner

SYSTEM AND METHOD FOR CONTROLLING ERRORS IN COMPUTED TOMOGRAPHY NUMBER

CROSS-REFERENCE TO RELATED APPLICATIONS

N/A

STATEMENT REGARDING FEDERALLY SPONSORED RESEARCH

N/A

BACKGROUND

The present disclosure relates to systems and methods for medical image data preparation, acquisition, and/or reconstruction. More particularly, systems and method are provided for controlling errors in computed tomography (CT) numbers, for example, as can commonly occur at low or reduced energy levels.

In traditional computed tomography systems, an x-ray source projects a beam that is collimated to lie within an X-Y plane of a Cartesian coordinate system, termed the "imaging plane." The x-ray beam passes through the object being imaged, such as a medical patient, and impinges upon an array of radiation detectors. The intensity of the radiation received by each detector element is dependent upon the attenuation of the x-ray beam by the object and each detector element produces a separate electrical signal that relates to the attenuation of the beam. The linear attenuation coefficient is the parameter that describes how the intensity of the x-rays changes when passing through an object. Often, the "mass attenuation coefficient" is utilized because it factors out the dependence of x-ray attenuations on the density of the material. The attenuation measurements from all the detectors are acquired to produce the transmission map of the object.

The source and detector array in a conventional CT system are rotated on a gantry within the imaging plane and around the object so that the projection angle at which the x-ray beam intersects the object constantly changes. A group of x-ray attenuation measurements from the detector array at a given angle is referred to as a "view" and a "scan" of the object. These views are collected to form a set of views made at different angular orientations during one or several revolutions of the x-ray source and detector. In a two dimensional (2D) scan, data is processed to construct an image that corresponds to a 2D slice taken through the object. The prevailing method for reconstructing an image from 2D data is referred to in the art as the filtered backprojection (FBP) technique. This process converts the attenuation measurements from a scan into integers called "CT numbers" or "Hounsfield units", which are used to control the brightness of a corresponding pixel on a display.

Over the past 15 years, much effort has been committed to lowering radiation dose for x-ray CT imaging due to the potential cancer risks associated with the use of ionizing radiation in CT. Many efforts have been made to develop and commercialize systems and methods that enable low-dose CT imaging. Primarily, this has yielded noise-reduction algorithms that seek to reduce the inevitable decreases in SNR as dose is decreased. However, CT hardware with improved radiation dose efficiency, primarily x-ray detectors such as photon counting detectors, have also been studied and developed to enable low dose CT imaging. Photon counting detector CT (PCD-CT) has been featured as one of the most important advances in low dose CT imaging due to its powerful noise rejection functionality in addition to other advantages such as spectral CT imaging capability. Currently, PCD-CT has been developed by major CT manufacturers for preclinical and clinical evaluations. In PCD-CT, the reduction of radiation exposure also helps to alleviate one of the technical challenges, pulse pileup, which is more severe at higher exposure levels.

When the radiation dose in CT imaging is lowered, not only are noise levels and photon starvation noise streaks elevated, but the CT number also becomes more and more inaccurate (i.e., CT numbers are more severely biased when radiation exposure level is reduced). This CT number bias issue has been reported for both regular CT with standard FBP reconstruction and low dose CT with iterative image reconstruction algorithms. For these applications, inaccuracies (i.e. biases) in the CT number can lead to misdiagnosis, mistreatment, and other detrimental clinical consequences.

The inaccuracy of CT numbers is easily confused with the inaccuracies caused by obvious image artifacts. This is one of the reasons that CT number bias issues are often overlooked in the CT imaging community. It is important to note that CT number bias issues are intrinsically rooted in the statistical nature of photons and the standard image formation process that has been used for the past 50 years in medical CT practices. In the current standard medical CT image formation process, after CT data are acquired, a log-transform is applied to generate the sinogram data, then an image reconstruction algorithm is applied to reconstruct the CT images. However, there is a fundamental flaw in this image formation process. That is, the log-transform itself is a statistically biased estimator, meaning that the statistical mean of the log-transformed data is different from the log-transform of the statistical mean of the data. In other words, different data processing orders (mean-log and log-mean) result in different results.

In medical CT, to avoid excessive radiation dose to patients and to shorten the prolonged data acquisition time, one cannot take the log-mean since there is no statistical mean of the measured patient data available. This constraint in practical medical CT data acquisitions forces us to take the logarithmic transform of the single sample of the measured CT data and then images are reconstructed from the log-transformed sinogram data. Fortunately, this difference is often negligible when the x-ray exposure level is relatively high (i.e. in normal radiation dose CT imaging practices). However, statistical bias becomes exponentially exacerbated in low dose CT imaging and it becomes a factor that must be addressed. Unlike artifact-related issues, for which a plethora of correction methods exist, there is no correction method available to address the statistical bias in standard FBP-based CT images.

Thus, it would be desirable to have systems and methods for managing or overcoming inaccuracy of CT numbers, for example, to improve image quality and/or facilitate dose reductions.

SUMMARY

The present disclosure provides systems and methods that overcome the aforementioned drawbacks by protect against the results of inaccuracies in CT numbers. In one non-limiting example, a system and method is provided for correcting bias in CT data. As one example, a method is provided for determining a photon count for given sinogram data and generating unbiased sinogram data from the sinogram data using an unbiased estimator and the photon count. Then, the unbiased CT data can be reconstructed into a CT image that otherwise would be degraded by the bias in the CT data, such as at a reduced or low dose.

In accordance with one aspect of the disclosure, a method is provided for creating computed tomography (CT) images. The method includes acquiring or accessing sinogram data and determining a photon count for the sinogram data. The method further includes generating unbiased sinogram data from the sinogram data using an unbiased estimator and the photon count and reconstructing a CT image from the unbiased sinogram data.

In accordance with another aspect of the disclosure, a computed tomography (CT) medical imaging system is provided that includes an x-ray source configured to deliver x-rays to an object as the x-ray source is rotated about the object and a detector having a plurality of detector elements configured to receive the x-rays and generate sinogram data therefrom. The system also includes a controller configured to control the x-ray source to deliver the x-rays and to receive the sinogram data from the detector and a processor. The processor is configured to determine a photon count for the sinogram data for a plurality of detector elements, generate unbiased sinogram data from the sinogram data using an unbiased estimator and the photon count, and reconstruct a CT image from the unbiased sinogram data.

In accordance with one other aspect of the disclosure, a method is provided that includes controlling a computed tomography system to acquire biased sinogram data ($y_i$) and determining a photon count ($N_i$) from the sinogram data. The method also includes generating unbiased sinogram data ($\tilde{y}_i$) using at least one of:

$$\tilde{y}_i = y_i - \frac{1}{2N_i} + \frac{1}{12N_i^2}$$

$$\tilde{y}_i = y_i - \frac{1}{2N_i} + \frac{1}{12N_i^2} - \frac{1}{120N_i^4}; \text{ or}$$

$$\tilde{y}_i = y_i - \frac{1}{2N_i} + \frac{1}{12N_i^2} + \frac{0}{N_i^3} - \frac{1}{120N_i^4} + \frac{0}{N_i^5} + \frac{1}{252N_i^6};$$

wherein i increments for each of a plurality of elements of a detector used to acquire the sinogram data. The method also includes reconstructing an image from the unbiased sinogram data.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
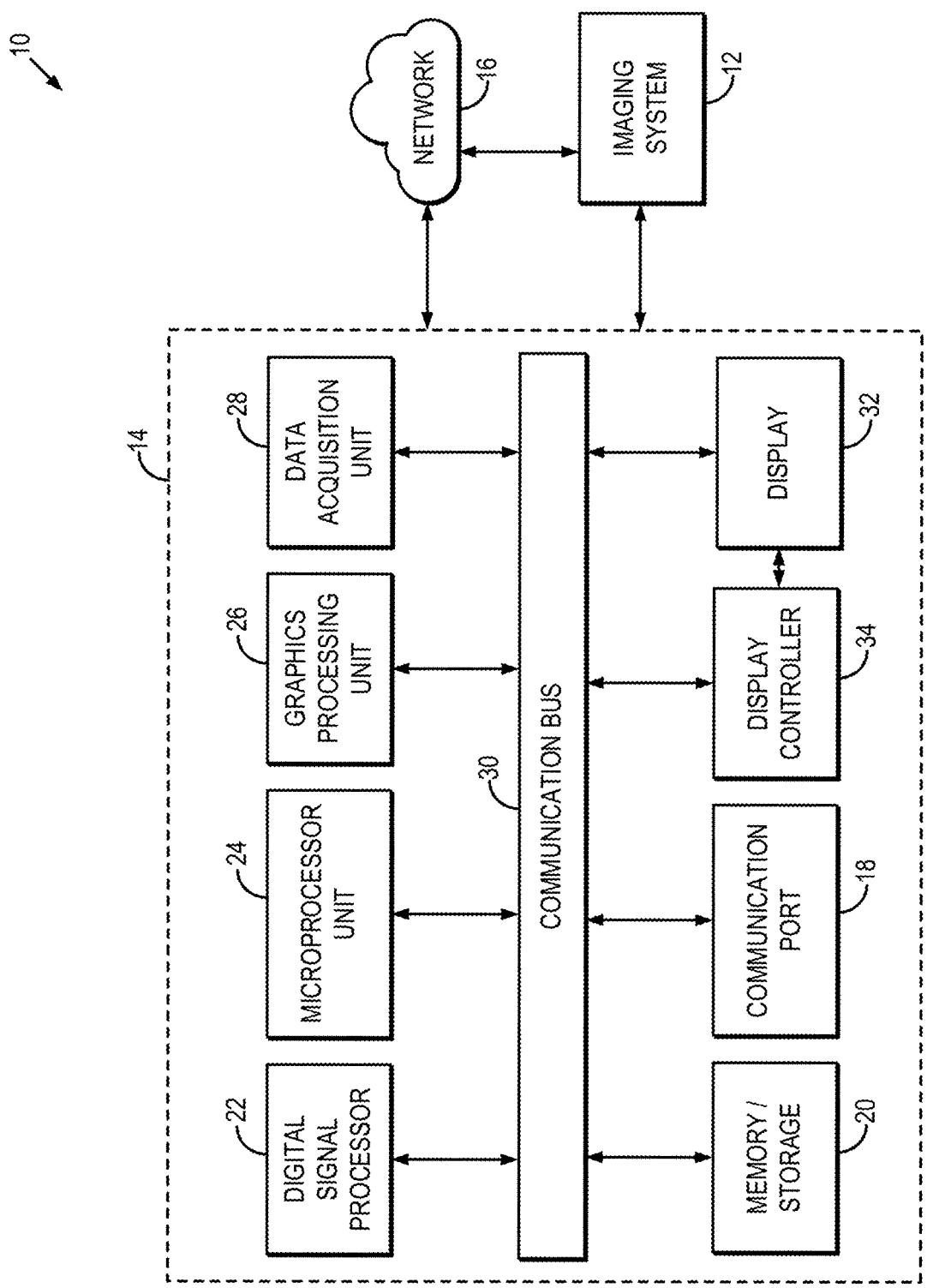
FIG. 1 is a schematic diagram of an example computer system that can be configured to implement the methods described herein.

Referring now to FIG. 1, a block diagram of an example system 10 is provided that can be configured to carry out techniques, methods, and processes accordance with the present disclosure. The system may include an imaging system 12 that is coupled to a computer system 14. The coupling of the imaging system 12 to the computer system 14 may be a direct or dedicated network connection, or may be through a broad network 16, such as an intranet or the Internet.

The computer system 14 may be a workstation integrated with or separate from the medical imaging systems 12 or a variety of other medical imaging systems, including, as non-limiting examples, computed tomography (CT) system, magnetic resonance imaging (MRI) systems, positron emission tomography (PET) systems, single photon emission computed tomography (SPECT) systems, and the like. Furthermore, the computer system 14 may be a workstation integrated within the medical imaging system 12 or may be a separate workstation or mobile device or computing system. To this end, the following description of particular hardware and configurations of the hardware of the example computer system 14 is for illustrative purposes. Some computer systems may have varied, combined, or different hardware configurations.

Medical imaging data acquired by the medical imaging system 12 or other imaging system can be provided to the computer system 14, such as over the network 16 or from a storage device. To this end, the computer system 14 may include a communications port or other input port 18 for communication with the network 16 and system coupled thereto. Also, the computer system 14 may include memory and storage capacity 20 to store and access data or images.

In some configuration, computer system 14 may include one or more processing systems or subsystems. That is, the computer system 14 may include one or more physical or virtual processors. As an example, the computer system 14 may include one or more of a digital signal processor (DSP) 22, a microprocessor unit (MPU) 24, and a graphics processing unit (GPU) 26. If the computer system 14 is integrated into the medical imaging system, a data acquisition unit 28 may be connected directly to the above-described processor(s) 22, 24, 26 over a communications bus 30, instead of communicating acquired data or images via the network 16. As an example, the communication bus 30 can be a group of wires, or a hardwire used for switching data between the peripherals or between any component, such as the communication buses described above.

The computer system 14 may also include or be connected to a display 32. To this end, the computer system 14 may include a display controller 34. The display 32 may be a monitor connected to the computer system 14 or may be integrated with the computer system 14, such as in portable computers or mobile devices.

Figure 2A:
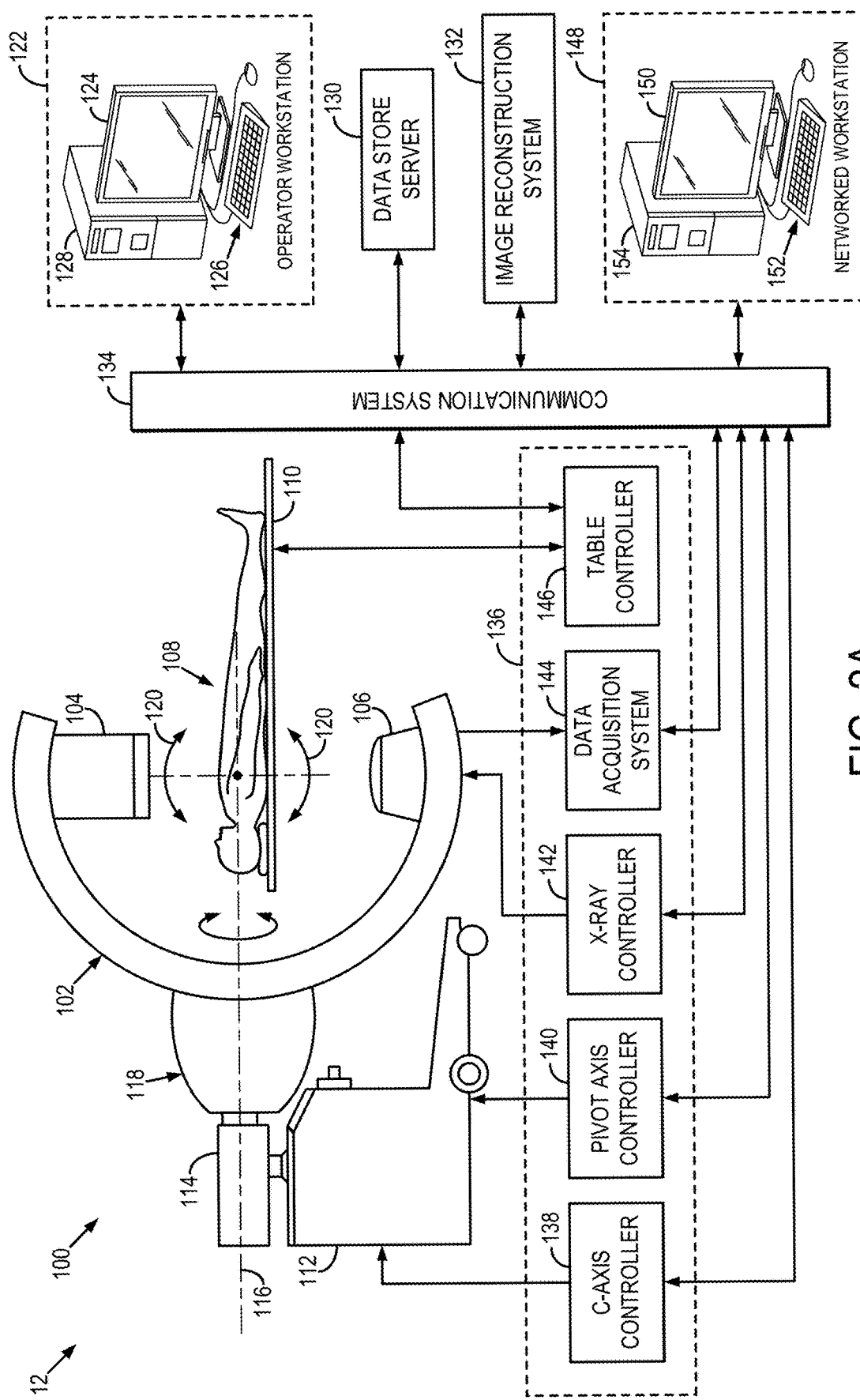
FIG. 2A is a schematic diagram of a C-arm x-ray computed tomography (CT) imaging system configured in accordance with the present disclosure.
Figure 2B:
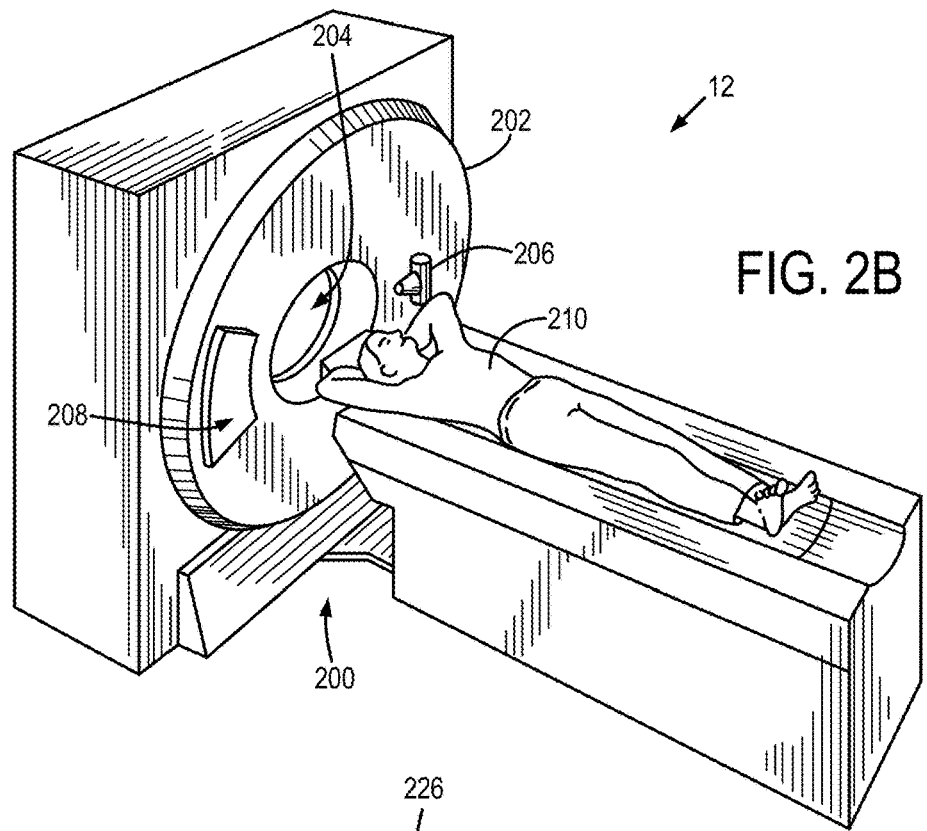
FIG. 2B is a perspective view of an example of an x-ray computed tomography (CT) system.

Referring to FIG. 2A, one, non-limiting example of the imaging system 12 of FIG. 1 is provided. Specifically, in this example, a so-called "C-arm" x-ray imaging system 100 is illustrated for use in accordance with some aspects of the present disclosure. Such an imaging system is generally designed for use in connection with interventional procedures. Such systems stand in contrast to, for example, traditional computed tomography (CT) systems 200, such as illustrated in FIG. 2B, which may also serve as an example of the imaging system 12 of FIG. 1.

Referring again to FIG. 2A, the C-arm x-ray imaging system 100 includes a gantry 102 having a C-arm to which an x-ray source assembly 104 is coupled on one end and an x-ray detector array assembly 106 is coupled at its other end. The gantry 102 enables the x-ray source assembly 104 and detector array assembly 106 to be oriented in different positions and angles around a subject 108, such as a medical patient or an object undergoing examination, which is positioned on a table 110. When the subject 108 is a medical patient, this configuration enables a physician access to the subject 108.

The x-ray source assembly 104 includes at least one x-ray source that projects an x-ray beam, which may be a fan-beam or cone-beam of x-rays, towards the x-ray detector array assembly 106 on the opposite side of the gantry 102. The x-ray detector array assembly 106 includes at least one x-ray detector, which may include a number of x-ray detector elements. Examples of x-ray detectors that may be included in the x-ray detector array assembly 106 include flat panel detectors, such as so-called "small flat panel" detectors. Such a detector panel allows the coverage of a field-of-view of approximately twelve centimeters.

Together, the x-ray detector elements in the one or more x-ray detectors housed in the x-ray detector array assembly 106 sense the projected x-rays that pass through a subject 108. Each x-ray detector element produces an electrical signal that may represent the intensity of an impinging x-ray beam and, thus, the attenuation of the x-ray beam as it passes through the subject 108. In some configurations, each x-ray detector element is capable of counting the number of x-ray photons that impinge upon the detector. During a scan to acquire x-ray projection data, the gantry 102 and the components mounted thereon rotate about an isocenter of the C-arm x-ray imaging system 100.

The gantry 102 includes a support base 112. A support arm 114 is rotatably fastened to the support base 112 for rotation about a horizontal pivot axis 116. The pivot axis 116 is aligned with the centerline of the table 110 and the support arm 114 extends radially outward from the pivot axis 116 to support a C-arm drive assembly 118 on its outer end. The C-arm gantry 102 is slidably fastened to the drive assembly 118 and is coupled to a drive motor (not shown) that slides the C-arm gantry 102 to revolve it about a C-axis, as indicated by arrows 120. The pivot axis 116 and C-axis are orthogonal and intersect each other at the isocenter of the C-arm x-ray imaging system 100, which is indicated by the black circle and is located above the table 110.

The x-ray source assembly 104 and x-ray detector array assembly 106 extend radially inward to the pivot axis 116 such that the center ray of this x-ray beam passes through the system isocenter. The center ray of the x-ray beam can thus be rotated about the system isocenter around either the pivot axis 116, the C-axis, or both during the acquisition of x-ray attenuation data from a subject 108 placed on the table 110. During a scan, the x-ray source and detector array are rotated about the system isocenter to acquire x-ray attenuation projection data from different angles. By way of example, the detector array is able to acquire thirty projections, or views, per second.

The C-arm x-ray imaging system 100 also includes an operator workstation 122, which typically includes a display 124; one or more input devices 126, such as a keyboard and mouse; and a computer processor 128. The computer processor 128 may include a commercially available programmable machine running a commercially available operating system. The operator workstation 122 provides the operator interface that enables scanning control parameters to be entered into the C-arm x-ray imaging system 100. In general, the operator workstation 122 is in communication with a data store server 130 and an image reconstruction system 132. By way of example, the operator workstation 122, data store server 130, and image reconstruction system 132 may be connected via a communication system 134, which may include any suitable network connection, whether wired, wireless, or a combination of both. As an example, the communication system 134 may include both proprietary or dedicated networks, as well as open networks, such as the Internet.

The operator workstation 122 is also in communication with a control system 136 that controls operation of the C-arm x-ray imaging system 100. The control system 136 generally includes a C-axis controller 138, a pivot axis controller 140, an x-ray controller 142, a data acquisition system (DAS) 144, and a table controller 146. The x-ray controller 142 provides power and timing signals to the x-ray source assembly 104, and the table controller 146 is operable to move the table 110 to different positions and orientations within the C-arm x-ray imaging system 100.

The rotation of the gantry 102 to which the x-ray source assembly 104 and the x-ray detector array assembly 106 are coupled is controlled by the C-axis controller 138 and the pivot axis controller 140, which respectively control the rotation of the gantry 102 about the C-axis and the pivot axis 116. In response to motion commands from the operator workstation 122, the C-axis controller 138 and the pivot axis controller 140 provide power to motors in the C-arm x-ray imaging system 100 that produce the rotations about the C-axis and the pivot axis 116, respectively. For example, a program executed by the operator workstation 122 generates motion commands to the C-axis controller 138 and pivot axis controller 140 to move the gantry 102, and thereby the x-ray source assembly 104 and x-ray detector array assembly 106, in a prescribed scan path.

The DAS 144 samples data from the one or more x-ray detectors in the x-ray detector array assembly 106 and converts the data to digital signals for subsequent processing. For instance, digitized x-ray data are communicated from the DAS 144 to the data store server 130. The image reconstruction system 132 then retrieves the x-ray data from the data store server 130 and reconstructs an image therefrom. The image reconstruction system 130 may include a commercially available computer processor, or may be a highly parallel computer architecture, such as a system that includes multiple-core processors and massively parallel, high-density computing devices. Optionally, image reconstruction can also be performed on the processor 128 in the operator workstation 122. Reconstructed images can then be communicated back to the data store server 130 for storage or to the operator workstation 122 to be displayed to the operator or clinician.

The C-arm x-ray imaging system 100 may also include one or more networked workstations 148. By way of example, a networked workstation 148 may include a display 150; one or more input devices 152, such as a keyboard and mouse; and a processor 154. The networked workstation 148 may be located within the same facility as the operator workstation 122, or in a different facility, such as a different healthcare institution or clinic.

The networked workstation 148, whether within the same facility or in a different facility as the operator workstation 122, may gain remote access to the data store server 130, the image reconstruction system 132, or both via the communication system 134. Accordingly, multiple networked workstations 148 may have access to the data store server 130, the image reconstruction system 132, or both. In this manner, x-ray data, reconstructed images, or other data may be exchanged between the data store server 130, the image reconstruction system 132, and the networked workstations 148, such that the data or images may be remotely processed by the networked workstation 148. This data may be exchanged in any suitable format, such as in accordance with the transmission control protocol (TCP), the Internet protocol (IP), or other known or suitable protocols.

Figure 2C:
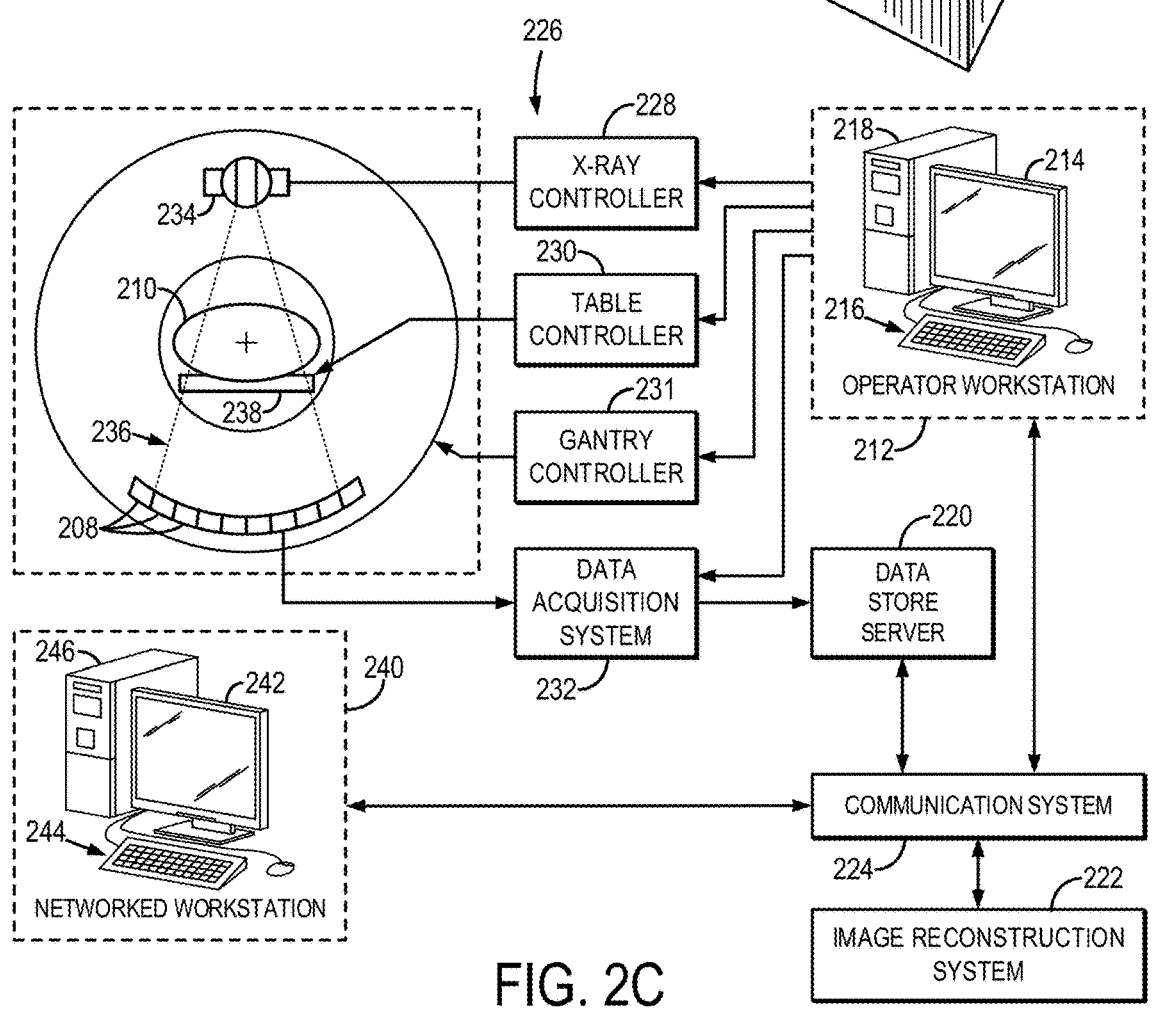
FIG. 2C is a block diagram of CT system, such as illustrated in FIG. 2B.

Similarly, referring to FIGS. 2B and 2C, the imaging system 12 may include a traditional CT system 200, which includes a gantry 202 that forms a bore 204 extending therethrough. In particular, the gantry 202 has an x-ray source 206 mounted thereon that projects a fan-beam, or cone-beam, of x-rays toward a detector array 208 mounted on the opposite side of the bore 204 through the gantry 202 to image the subject 210.

The CT system 200 also includes an operator workstation 212, which typically includes a display 214; one or more input devices 216, such as a keyboard and mouse; and a computer processor 218. The computer processor 218 may include a commercially available programmable machine running a commercially available operating system. The operator workstation 212 provides the operator interface that enables scanning control parameters to be entered into the CT system 200. In general, the operator workstation 212 is in communication with a data store server 220 and an image reconstruction system 222 through a communication system or network 224. By way of example, the operator workstation 212, data store sever 220, and image reconstruction system 222 may be connected via a communication system 224, which may include any suitable network connection, whether wired, wireless, or a combination of both. As an example, the communication system 224 may include both proprietary or dedicated networks, as well as open networks, such as the Internet.

The operator workstation 212 is also in communication with a control system 226 that controls operation of the CT system 200. The control system 226 generally includes an x-ray controller 228, a table controller 230, a gantry controller 231, and a data acquisition system (DAS) 232. The x-ray controller 228 provides power and timing signals to the x-ray module(s) 234 to effectuate delivery of the x-ray beam 236. The table controller 230 controls a table or platform 238 to position the subject 210 with respect to the CT system 200.

The DAS 232 samples data from the detector 208 and converts the data to digital signals for subsequent processing. For instance, digitized x-ray data are communicated from the DAS 232 to the data store server 220. The image reconstruction system 222 then retrieves the x-ray data from the data store server 220 and reconstructs an image therefrom. The image reconstruction system 222 may include a commercially available computer processor, or may be a highly parallel computer architecture, such as a system that includes multiple-core processors and massively parallel, high-density computing devices. Optionally, image reconstruction can also be performed on the processor 218 in the operator workstation 212. Reconstructed images can then be communicated back to the data store server 220 for storage or to the operator workstation 212 to be displayed to the operator or clinician.

The CT system 200 may also include one or more networked workstations 240. By way of example, a networked workstation 240 may include a display 242; one or more input devices 244, such as a keyboard and mouse; and a processor 246. The networked workstation 240 may be located within the same facility as the operator workstation 212, or in a different facility, such as a different healthcare institution or clinic.

The networked workstation 240, whether within the same facility or in a different facility as the operator workstation 212, may gain remote access to the data store server 220 and/or the image reconstruction system 222 via the communication system 224. Accordingly, multiple networked workstations 240 may have access to the data store server 220 and/or image reconstruction system 222. In this manner, x-ray data, reconstructed images, or other data may be exchanged between the data store server 220, the image reconstruction system 222, and the networked workstations 212, such that the data or images may be remotely processed by a networked workstation 240. This data may be exchanged in any suitable format, such as in accordance with the transmission control protocol (TCP), the Internet protocol (IP), or other known or suitable protocols.

Using the above-described systems, systems and methods are provided for correcting bias in CT data. As one example, a method is provided for determining a photon count for given sinogram data and generating unbiased sinogram data from the sinogram data using an unbiased estimator and the photon count. Then, the unbiased CT data can be reconstructed into a CT image that otherwise would be degraded by the bias in the CT data, such as at a reduced or low dose. For example, the systems and methods provided can provide clinically viable CT images, even at reduced doses of less than 1 mGy.

Before turning to these systems and methods, it is advantageous to consider the root cause of bias in CT images. In this explanation, the symbols $(\cdot)$, $E(\cdot)$, and $\langle(\cdot)\rangle$ interchangeably to denote the mathematical expectation of a random variable. For example, $\bar{N}_{io}$ denotes the expected x-ray photon number received by the ith detector element when there is no object present in the x-ray beam (i.e., air scan); $\bar{N}_i$ denotes the actual photon number received by the ith detector element when an image object is present in the beam. Based on the Beer-Lambert law, $\bar{N}_i$ is related to $\bar{N}_{i0}$ and the x-ray linear attenuation coefficient of the image object μ by:

$$\bar{N}_i = \bar{N}_{i0} \int_0^{E_{max}} dE\Omega(E) e^{-\int_{l_i} dl \mu(\vec{x}, E)}; \quad (1)$$

$$= \bar{N}_{i0} e^{-\int_{l_i} dl \mu(\vec{x}, \in_i)}; \quad (2)$$

where $\Omega(E)$ denotes the normalized effective x-ray spectrum, $\in_i \in [0, E_{max}]$, l represents the spatial path of the x-ray, and $\vec{x}$ is the spatial location in the image object. From equation (1) to equation (2), the Mean Value Theorem is used. By taking the logarithmic transform of equation (2), the following well-known fundamental CT imaging equation can be obtained:

$$p_i = \ln\left(\frac{\bar{N}_{i0}}{\bar{N}_i}\right) = \int_{l_i} dl\mu(\vec{x}, \in_i); \quad (3)$$

where $p_i$ is the projection along point, i. As pointed out by both Dr. Cormack and Sir Hounsfield in their 1979 Nobel Lectures, equation (3) has been used to formulate the CT reconstruction problem ever since CT was invented. Despite its wide use, equation (3) has an often overlooked issue. Specifically, this formulation in equation (3) is not intrinsically compatible with clinical CT acquisitions. Note that to get the log-normalized projection data, $p_i$, equation (2) requires the knowledge of both $\bar{N}_{i0}$ and $\bar{N}_i$. While $\bar{N}_{i0}$ can be estimated via a large number of repeated air scans and ensemble averaging, in clinical CT imaging, one cannot repeatedly scan a patient to get $\bar{N}_i$ due to constraints in radiation dose, tube cooling, and clinical throughput. Consequently, one has to rely on a single measurement photon number ($N_i$) to generate the so-called sinogram data, $y_i$, for CT reconstruction:

$$y_i := \ln\left(\frac{\bar{N}_{i0}}{N_i}\right). \quad (4)$$

The replacement of the actual photon number for each detector element with the actual object to be imaged present, $\bar{N}_i$ by a single measurement of photon number, $N_i$ has been implemented in almost all clinical CT scanners for the past 50 years. The inconsistency between the deterministic pi in equation (3) and the intrinsically stochastic data $y_i$ in equation (4) gives rise to multiple problems. First, there is the well-known noise issue, particularly, when the dose (and, thus, $\bar{N}_i$) is low. Another problem that has been largely overlooked is that $y_i$ is a statistically biased estimator of the desired projection data, $p_i$.

$$\langle y_i \rangle = \ln \bar{N}_{io} - \langle \bar{N}_i \rangle \neq p_i = \ln \bar{N}_{io} - \ln \bar{N}_i \quad (5).$$

The present disclosure recognizes that the difference between $\langle y_i \rangle$ and $p_i$ is defined as the statistical bias of the sinogram data:

$$\text{Bias}_{y_i} = \langle y_i \rangle - p_i \ln \bar{N}_i - \langle \ln \bar{N}_i \rangle \quad (6).$$

For a random variable N that follows the Poisson distribution, its moment-generating function (MGF) is a useful tool to calculate high-order moments. The MGF is given by:

$$M_N(s) := E\{e^{sN}\} = \sum_{n=0}^{\infty} e^{sn} e^{-\lambda} \frac{\lambda^n}{n!} = e^{\lambda[e^s - 1]}; \quad (6a)$$

where $E\{\cdot\}$ denotes mathematical expectation, $\lambda = E\{N\}$ denotes the expected value of the random variable N, s is a variable of the MGF that calculates the moments as shown in equation (6b), and n is the index of summation. Using the above MGF, the kth-order moment $N^k$ can be readily calculated by taking the kth-order derivative of the moment generating function with respect to the parameters at s=0:

$$E\{N^k\} = \left.\frac{d^k M_N(s)}{ds^k}\right|_{s=0}; \quad (6b)$$

Once $E\{N^k\}$ is calculated, the kth-order central moments for $N^k$ can be calculated using the binomial theorem as follows:

$$E\{(N-\lambda)^k\} = \sum_{i=0}^{k} (-1)^i \frac{k!}{i!(k-i)!} E\{N^i\} \lambda^{k-i}. \quad (6c)$$

The following Table shows the calculated central moments of $N_k$ for k up to 10.

| THE EXPANDED FORM OF $E\{(N - \lambda)^k\}$ FOR $k \leq 10$. | |
|---|---|
| $E[(N - \lambda)]$ | 0 |
| $E[(N - \lambda)^2]$ | $\lambda$ |
| $E[(N - \lambda)^3]$ | $\lambda$ |
| $E[(N - \lambda)^4]$ | $\lambda(1 + 3\lambda)$ |
| $E[(N - \lambda)^5]$ | $\lambda(1 + 10\lambda)$ |
| $E[(N - \lambda)^6]$ | $\lambda(1 + 25\lambda + 15\lambda^2)$ |
| $E[(N - \lambda)^7]$ | $\lambda(1 + 56\lambda + 105\lambda^2)$ |
| $E[(N - \lambda)^8]$ | $\lambda(1 + 119\lambda + 490\lambda^2 + 105\lambda^3)$ |
| $E[(N - \lambda)^9]$ | $\lambda(1 + 246\lambda + 1918\lambda^2 + 1260\lambda^3)$ |
| $E[(N - \lambda)^{10}]$ | $\lambda(1 + 501\lambda + 6825\lambda^2 + 9450\lambda^3 + 945\lambda^4)$ |

The Taylor series of lnN around $N=\lambda$ is given by:

$$\ln N = \sum_{i=0}^{\infty} \frac{1}{i!} \left.\frac{d^i(\ln N)}{dN^i}\right|_{N=\lambda} (N-\lambda)^i \quad (6d)$$

$$= \ln \lambda + \sum_{i=1}^{\infty} (-1)^{i+1} \frac{1}{i\lambda^i} (N-\lambda)^i$$

As a result, the statistical bias of lnN can be readily calculated as follows:

$$\text{Bias}_{lnN} := E\{\ln N\} - \ln E\{N\} \quad (6e)$$

$$= E\{\ln N\} - \ln \lambda$$

$$= \sum_{i=1}^{\infty} (-1)^{i+1} \frac{1}{i\lambda^i} E\{(N-\lambda)^i\}$$

Using the tabulated central moments from the above table, the statistical bias of the random variable lnN is given by:

$$Bias_{lnN} = -\frac{1}{2\lambda} - \frac{5}{12\lambda^2} - \frac{3}{4\lambda^3} - \frac{251}{120\lambda^4} - O\left(\frac{1}{\lambda^5}\right); \quad (6f)$$

where $O$ is represents the coefficient for expansion of this series. This result, as will be discussed, can be used to guide construction of unbiased sinogram data. A a matter of fact, using equation (6), bias of the CT projection data defined in equation (4) can be calculated using the above result shown in equation (6f) as follows:

$$Bias_{y_i} = -Bias_{lnN_i} \quad (7)$$
$$= \frac{1}{2\bar{N}_i} + \frac{5}{12\bar{N}_i^2} + \frac{3}{4\bar{N}_i^3} + \frac{251}{120\bar{N}_i^4} + \ldots$$

Equation (7) shows that there exists a bias in the sinogram, if $N_i$ is only measured once and used for CT reconstruction and the magnitude of the bias increases monotonically when radiation dose (a quantity linearly proportional to $\bar{N}_i$) is reduced. When the biased sinogram data are used to reconstruct CT images, it is no surprise to observe bias in CT numbers for both FBP reconstruction and for most of the commercially available statistical model-based iterative reconstruction algorithms.

Though others have recognized this bias problem in CT number, it doesn't seem to indicate a way to solve such a fundamental problem with CT imaging. In its 50-year history, this bias has been present and accepted. For relatively high dose CT imaging, as indicated by the amount of bias shown in equation (7), the resulted CT number bias can be tolerated and accepted in practice, however, in the current movement of low dose CT imaging enabled by both CT scanner hardware and CT image reconstruction algorithms, this statistical bias shown in equation (7) becomes the bottleneck in low dose CT technological development. Without a systematical way to address this challenge, other efforts in low dose CT imaging will not lead to fruitful clinical outcome.

The present disclosure provides systems and methods to overcome this inherent bias problem in CT imaging. As will be described, an unbiased estimator of CT sinogram data can be developed. To develop this unbiased estimator, two additional realizations were utilized. First, the bias of the classical estimator of CT sinogram data (i.e., equation (4), which says $$y_i = \ln\left(\frac{\bar{N}_{i0}}{N_i}\right),$$

consists of a summation of terms, as shown in equation (7)

$$\left(\text{i.e., } \sum_{k=1}^{\infty} \frac{A_k}{N_i^k}\right).$$

Second, the statistical biases of the random variable $$\frac{1}{N_i^k}$$

is also a summation of terms $$\sum_{j=k+1}^{\infty} \frac{B_j}{N_i^j},$$

which has the same functional form as that of the biases of y, but with different coefficients, $B_j$.

That is, similar to the calculations of statistical bias of lnN, the statistical bias of the random variable $N^{-k}$ can also be calculated as:

$$Bias_{N^k} := \quad (7a)$$
$$E\{N^{-k}\} - (E\{N\})^{-k} = E\{N^{-k}\} - \lambda^{-k} = \frac{1}{\lambda^k}E\left\{\left(1 + \frac{N-\lambda}{\lambda}\right)^{-k}\right\} - \frac{1}{\lambda^k} =$$
$$\frac{1}{\lambda^k}\sum_{i=0}^{\infty}(-1)^i\frac{(k-1+i)!}{i!\,(k-1)!}E\left\{\left(\frac{N-\lambda}{\lambda}\right)^i\right\} - \frac{1}{\lambda^k} =$$
$$\sum_{i=0}^{\infty}\frac{(-1)^i}{\lambda^{i+k}}\frac{(k-1+i)!}{i!\,(k-1)!}E\{(N-\lambda)^i\}.$$

Using the above equation (7a) and the results in the table of mean values of Biases in the material basis of images provided below, the statistical bias of the random variable $N^{-k}$ can be readily calculated. The first four are:

$$Bias_{N^{-1}} = \frac{1}{\lambda^2} + \frac{2}{\lambda^3} + \frac{6}{\lambda^4} + O\left(\frac{1}{\lambda^5}\right) \quad (7b)$$
$$Bias_{N^{-2}} = \frac{3}{\lambda^3} + \frac{11}{\lambda^4} + O\left(\frac{1}{\lambda^5}\right)$$
$$Bias_{N^{-3}} = \frac{6}{\lambda^4} + O\left(\frac{1}{\lambda^5}\right)$$
$$Bias_{N^{-4}} = O\left(\frac{1}{\lambda^5}\right).$$

These results were then used to construct the unbiased CT sinogram data described hereafter.

Again, the present disclosure provides builds upon two important recognitions. First, the bias of the classical estimator of CT sinogram data (i.e., equation (4), which says $$y_i = \ln\left(\frac{\bar{N}_{i0}}{N_i}\right),$$

consists of a summation of terms, as shown in equation (7)

$$\left(\text{i.e., } \sum_{k=1}^{\infty} \frac{A_k}{N_i^k}\right).$$

Second, the statistical biases of the random variable $$\frac{1}{N_i^k}$$

is also a summation of terms $$\sum_{j=k+1}^{\infty} \frac{B_j}{N_i^j},$$

which has the same functional form as that of the biases of $y_i$ but with different coefficients, $B_j$. These two key observations suggest that it is possible to construct an unbiased estimator for CT projection data as:

$$y_i' = y_i + \sum_{k=1}^{\infty} \frac{C_k}{N_i^k} \qquad (8)$$

where the statistical bias in $y_i$ and the statistical biases of the terms $$\frac{C_k}{N_i^k}$$

in summation can be canceled out provided that the coefficients $C_k$ (k=1, 2, ...) are properly chosen. In practice, the summation can be truncated at the finite order K to ensure that the residual statistical bias is only up to the higher orders $$O\left(\frac{1}{N_i^{K+1}}\right).$$

As one non-limiting example, consider an explicit construction for the case of K=4. In this case:

$$y_i' = y_i + \frac{C_1}{N_i} + \frac{C_2}{N_i^2} + \frac{C_3}{N_i^3} + \frac{C_4}{N_i^4} \qquad (9)$$

For this estimator constructions, the corresponding statistical bias is given by:

$$Bias_{y_i'} = \qquad (10)$$

$$\langle y_i' \rangle - p_i = \langle y_i \rangle - p_i + \sum_{k=1}^{4} C_k \left\langle \frac{1}{N_i^k} \right\rangle = Bias_{y_i} + \sum_{k=1}^{4} C_k \left( \frac{1}{N_i^k} + Bias_{\frac{1}{N_i^k}} \right).$$

Using the result of $Bias_{y_i}$ in equation (7) and the calculated statistical biases of terms $$\frac{1}{N_i^k}$$

described above, the statistical bias of the newly constructed estimator of CT sinogram data in equation (9) is given as:

$$Bias_{y_i'} = \qquad (11)$$

$$\left(\frac{1}{2} + C_1\right)\frac{1}{N_i} + \left(\frac{5}{12} + C_1 + C_2\right)\frac{1}{N_i^2} + \left(\frac{3}{4} + 2C_1 + 3C_2 + C_3\right)\frac{1}{N_i^3} +$$

$$\left(\frac{251}{120} + 6C_1 + 11C_2 + 6C_3 + C_4\right)\frac{1}{N_i^4}.$$

Therefore, to cancel out the statistical bias in newly constructed CT sinogram data, $y_i$, as shown in equation (9), the coefficients $C_1$, $C_2$, $C_3$, $C_4$ need to be chosen to nullify the coefficients for the terms $$\frac{1}{N_i^k}$$

in equation (11). Recognizing this yields the following choices:

$$\begin{cases} C_1 = -\frac{1}{2}, \\ C_2 = \frac{1}{12}, \\ C_3 = 0, \\ C_4 = -\frac{1}{120}, \end{cases} \qquad (12)$$

The above choices of coefficients allow us to construct, up to the accuracy of $$O\left(\frac{1}{N_i^5}\right),$$

the unbiased estimator of pi as follows:

$$\tilde{y}_i = y_i - \frac{1}{2N_i} + \frac{1}{12N_i^2} - \frac{1}{120N_i^4}. \qquad (13)$$

Notably, this is only an example to show the process of how an unbiased estimator of the CT sinogram data can be obtained using the construction scheme presented herein. Other, for example, higher-order constructions can be utilized. As an example, the construction up to the 7th order as follows:

$$\tilde{y}_i = y_i - \frac{1}{2N_i} + \frac{1}{12N_i^2} + \frac{0}{N_i^3} - \frac{1}{120N_i^4} + \frac{0}{N_i^5} + \frac{1}{252N_i^6}. \qquad (14)$$

Thus, though non-limiting example, equations (13) and (14) reflect examples of a new paradigm for CT data. Thus, a first closed-form analytical constructions of unbiased CT sinogram data has been provided to address the statistical bias problem in CT, including low-dose PCD-CT, by using Ni directly. This construct is particularly important as dose is decreased because, as shown above, the magnitude of the correction terms increases with lower radiation dose.

The present disclosure recognizes that, in many practical applications, it may be sufficiently accurate to only keep, for example, the first two terms in the corrected sinogram data, namely:

$$\tilde{y}_i = y_i - \frac{1}{2N_i} + \frac{1}{12N_i^2}; \quad (15)$$

which will be further detailed below and illustrated with respect to experimental results. Additionally, the two-term approximation in equation (15) is often accurate up to the order of $$O\left(\frac{1}{N^4}\right)$$

due to the fact that the coefficient of the third order term, $C_3^i$, equals 0 as shown in equation (12).

Figure 3:
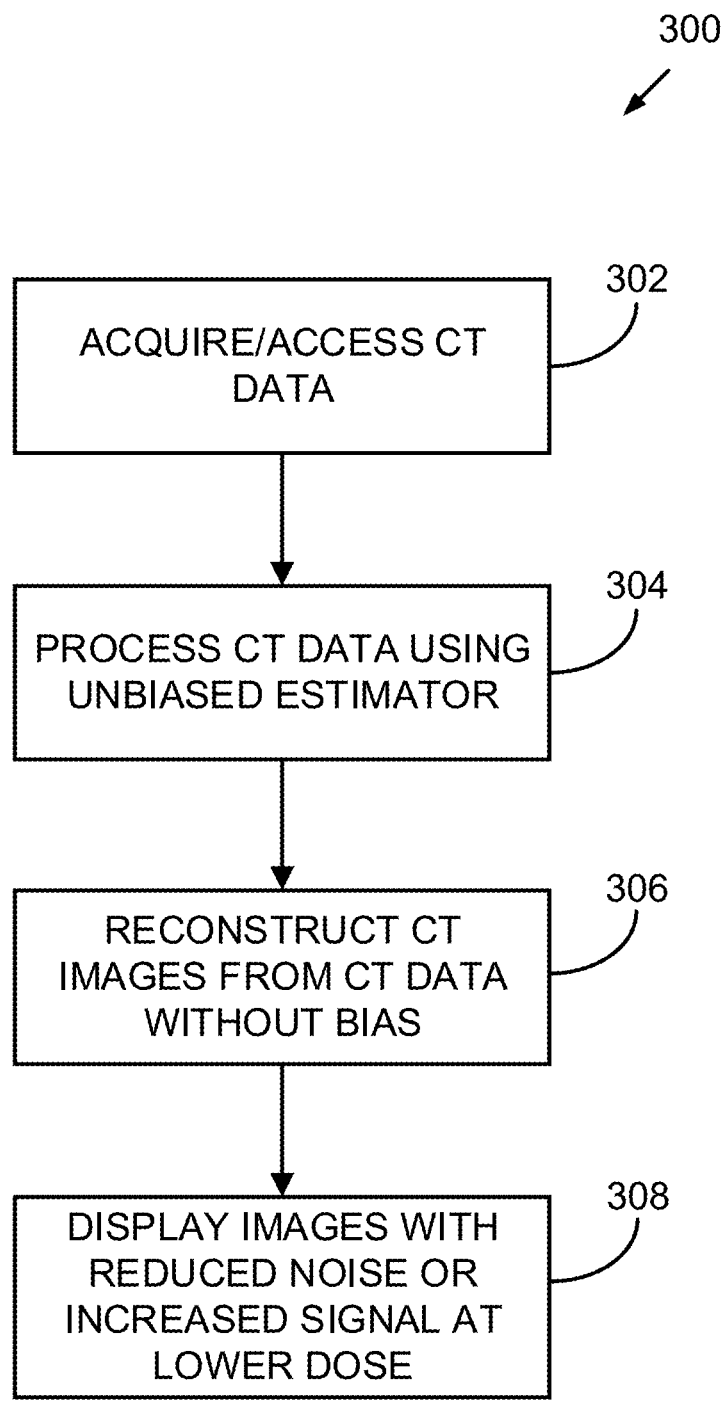
FIG. 3 is a flow chart setting forth some example steps of a process for creating unbiased CT images in accordance with the present disclosure.

Referring now to FIG. 3, a flow chart is provided setting forth one, non-limiting example of a process 300 for creating CT images using the above-described systems and methods. The process begins by acquiring or accessing CT data at process block 302. That is the CT data may be acquired from the object or subject to begin the process, or the CT data may have been previously acquired and stored, such that it is now access at process block 302.

At process block 304, an unbiased estimator is utilized to process the CT data. As described above, the unbiased estimator may take a variety of forms, as may the process for using the unbiased estimator. For example, as described above, if dose was of no concern, one could, in theory, measure the actual photon number received by the ith detector element when an image object is present in the beam ($N_i$). Of course, dose always has been and always is a concern. Thus, a closed-form, analytical constructions of unbiased CT sinogram data, such as described above in equations (13), (14), or (15) may be used to facilitate the use of single measurement photon number ($N_i$) without imparting bias to the CT data.

Then, at process block 306, the CT data may be reconstructed into images, such as using FBP or compressed sensing, or another reconstruction technique. Finally, the images may be displayed, which will have reduced noise and/or increased signal when compared to traditional images having bias, particularly at lower doses, as described above.

EXPERIMENTS

To validate the above-described systems and methods for constructing the unbiased sinogram estimator and quantify any residual biases in both the sinogram domain and the reconstructed CT image domain, the following experimental methods and materials were used.

The experimental data were acquired using a benchtop PCD-CT system. This system was equipped with a cadmium telluride (CdTe)-based PCD (XC-Hydra FX50, Direct Conversion AB, Sweden) with 5120x60 active pixels, each of which has a physical size of 0.1 mm×0.1 mm. The PCD was equipped with two adjustable energy thresholds and its CdTe layer had a thickness of 0.75 mm. The PCD was operated under the anti-coincidence (a.k.a. anti-charge sharing) mode. No prospective detector pixel binning was applied. The x-ray source was a rotating-tungsten anode diagnostic x-ray tube (G1952 with B-180H housing, Varian Medical Systems, Inc., UT, USA). During all experimental acquisitions, the tube was operated under the continuous fluoroscopic mode at 120 kV and 2 mA and with the small (0.6 mm) focal spot. Other major components of the PCD-CT system include an 80 kW high frequency generator (Indico100, CPI Inc., Ontario, Canada), a square-field manual collimator, a 0.25 mm copper beam filter, and a motorized rotary stage. The source-to-detector distance and source-to-isocenter distance of the system are 103.4 cm and 57.2 cm, respectively.

Figure 4:
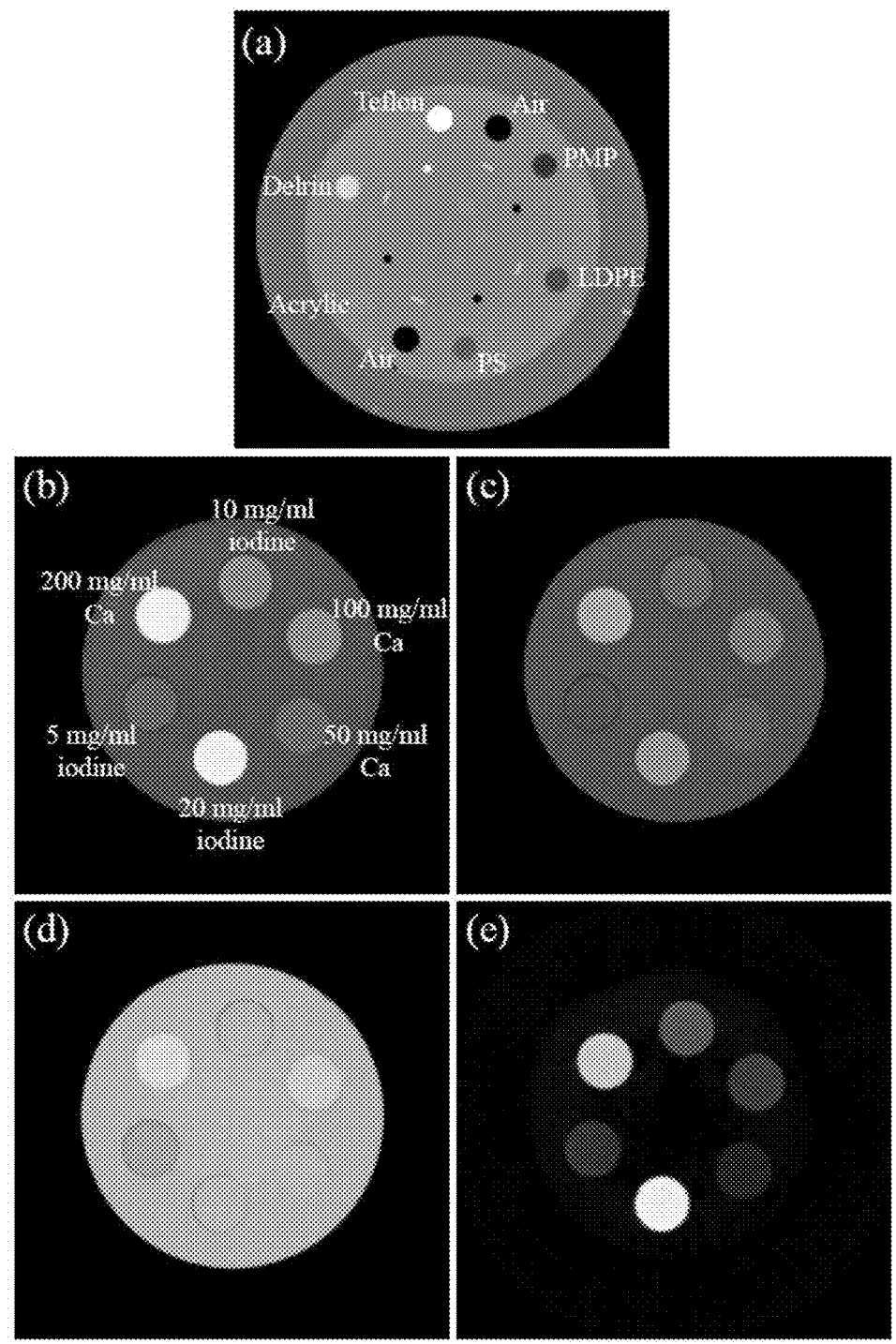
FIG. 4 is a set of correlated images of two physical phantoms used to demonstrate some aspects of the present disclosure.

Two image objects were used in this work: the first one is the CTP404 module in a Catphan600 phantom (The Phantom Laboratory, NY, USA) with an outer diameter of 20 cm. This phantom module contains multiple cylindrical inserts of different materials as shown in FIG. 4, as shown in panel (a). In the second image object, six calcium- or iodine-containing rods from the Gammex Dual Energy CT (DECT) Characterization Phantom (Model 472, Gammex Inc., WI, USA) were placed in a 16 cm diameter acrylic cylinder. The calcium or iodine concentrations of the six rods are specified in FIG. 4 in panel (b). During PCDCT scans of the DECT phantom, the PCD was operated under the dual-energy mode with both low- and high-energy threshold controllers activated and set at 15 keV and 63 keV, respectively. For scans of the Catphan600 phantom, the PCD was operated under the non-spectral mode with only the low energy threshold activated and set at 15 keV to reject electronic noise. Panel (c) shows high energy (HE) bin image CT image. Panel (d) shows a water basis image. Panel (e) is an iodine basis image.

The PCD-CT acquisitions of each phantom were performed at 10 different radiation dose levels. The dose level was adjusted by changing the scan time (and thus the mAs) of each PCD-CT acquisition. The dose level was quantified using the metric of the weighted CT Dose Index (CTDIw) and experimentally measured using a 16-cm CTDI phantom and a 100-mm pencil chamber (Model 10X6-3CT, Radcal Cop., CA, USA). The highest dose level (48 mGy), referred to as the reference or 100% dose level, was determined based on the standard-of-practice CTDI (CTDIw value of typical clinical head CT exams at our institution). Twenty repeated scans were performed at the 100% dose level for each phantom in order to establish the gold standards for pi in equation (3) and for the CT numbers. The other nine reduced-dose levels range from 9 to 36 mGy, yielding a dose reduction factor between 25% to 81%. Three repeated scans were performed at each reduced dose level. Across all dose levels, the number of projection view angles was fixed at 1,200 (uniformly distributed over each 360 degree full scan). For each dose level, an ensemble of 1,200 air-scan projections were recorded and averaged to obtain $\overline{N}_{i0}$.

Importantly, when radiation dose level is reduced, some PCD pixels, particularly those behind highly attenuating regions of an image object, may register zero count (i.e. $N_i=0$). For example, in a raw projection image of the Catphan600 phantom, 30 of the 5120×60 detector pixels showed zero count. Special attention should be paid to zero-count pixels, otherwise one will run into the division-by-zero problem when implementing the proposed bias correction scheme shown in equations (13)-(15). Even for the standard log-normalization process without the proposed bias correction, equation (4) indicates that special treatments of zero-count pixels are needed.

Figure 5:
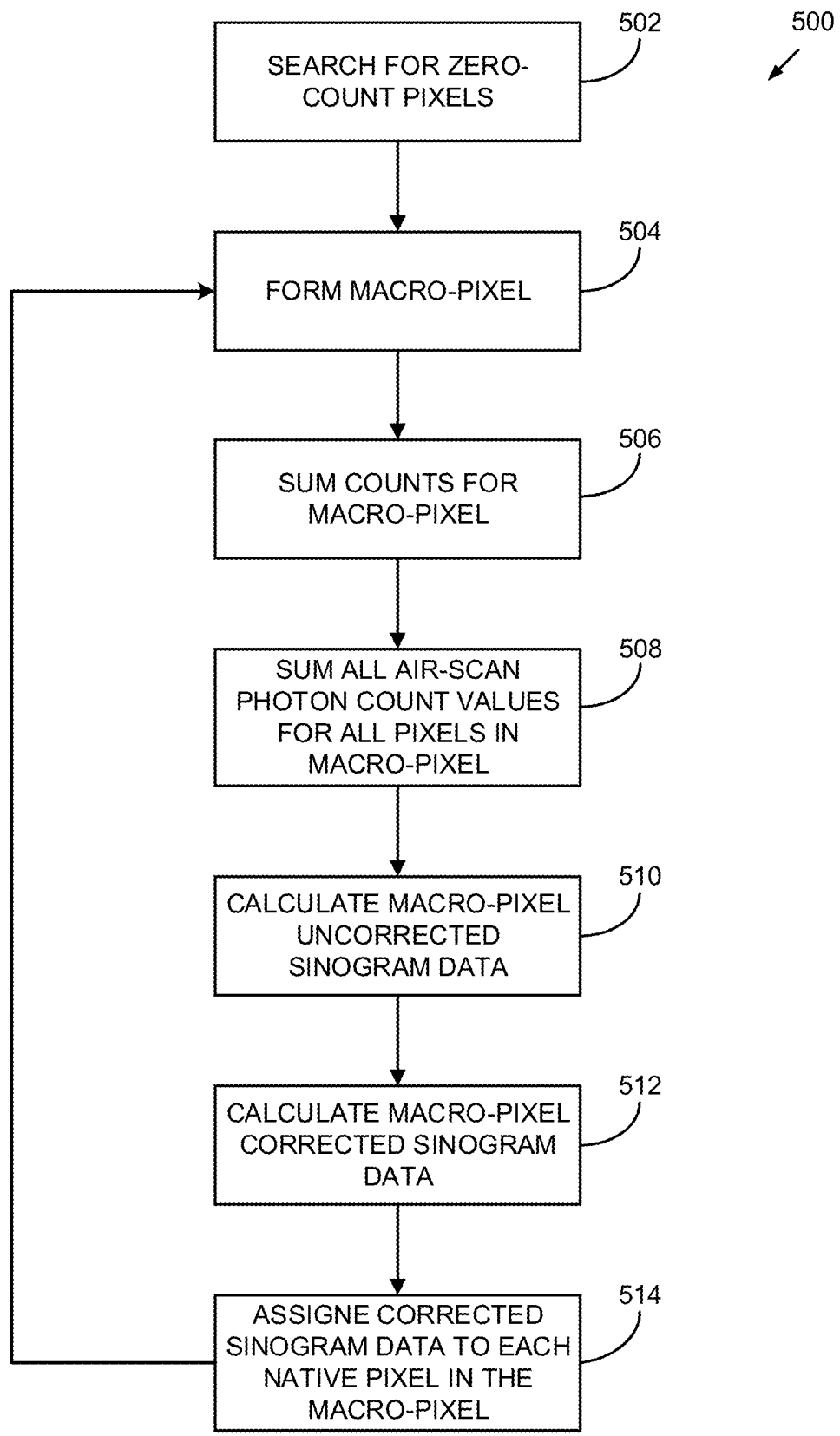
FIG. 5 is a flow chart setting forth some example steps of a process for creating unbiased CT images in accordance with the present disclosure in the presence of zero counts from detector elements.

Thus, the present disclosure also provides systems and methods for addressing this issue. For example, the present disclosure provides a procedure 500 for zero-counting pixels corrected using a sub-procedure illustrated in FIG. 5. The procedure 500 may be used with the process described with respect to FIG. 3. The process begins at process block 302 by searching and identifying the locations of all zero-count pixels in the object-present raw-count projection data. Then, at process block 504, for each zero-count pixel location, a "macro pixel" can be formed locally to include that pixel and neighboring pixels, for example, 3 neighbors. In this non-limiting example of 3 neighbors, the raw counts of these 2×2 native pixels can be summed together to obtain the count, $N_0'$ of that macro pixel at process block 506. In the unlikely case where all native pixels within a macro pixel have zero-counts, the size of the macro pixel can be further expanded until $N_0'>0$.

At process block 508, for each macro pixel location, the corresponding air-scan count value, $\overline{N}_0'$, by summing $\overline{N}_0$ of all native pixels within the macro pixel. At process block 510, macro-pixel uncorrected sinogram data is calculated as $$y_i' = \ln\left(\frac{\overline{N}_0'}{N'}\right).$$

Then, at process block 512, macro-pixel corrected sinogram data is calculated as $$\tilde{y}_i = y^i - \frac{1}{2N'} + \frac{1}{12N_i'^2}.$$

At process block 514, the calculated value of $\tilde{y}$ is assigned to each native pixel within the macro-pixel. The process is then repeated until all zero-count pixel locations have been processed.

Since the pixel binning is applied only to zero-count pixels, its impact on spatial resolution or partial volume averaging is minimal compared to global detector pixel binning. Note that the bias correction scheme in equation (15) is applicable to the macro-pixels, because the summation of PCD counts are still Poisson-distributed. The average count of the native pixels would not be desirable to use in a macro-pixel because the average count is not Poisson-distributed and, thus, the correction coefficients would need to be modified. As a second note, at process block 512, $\tilde{y}$ is preferably assigned to all native pixels within each macro-pixel, instead of only to those native pixels with zero-count, which will change the expected value of $\tilde{y}$ for the macro-pixel and, thus, create a new source of bias.

Methods to determine statistical biases in the sinogram domain where also experimentally considered. In particular, referring to FIG. 6, a graphic illustration is provided to show a process for experimental comparison of biased CT data with unbiased CT data. For each phantom, a reference sinogram, p, 600 was generated by performing ensemble averaging 602 of the raw detector counts from 20 repeated acquisitions 604 at the 100% dose level to get N before a log-normalization was applied 600. The reference sinogram 600 was used to produce a reference CT image 606.

A plurality of reduced dose acquisitions 608 were also acquired. At each reduced dose level, equation (4) was applied to the raw detector count to generate the uncorrected sinogram, y, 610. This was then reconstructed using filter backprojection into uncorrected CT images 612. This was then assembled into an uncorrected ensemble image 614 averaging the uncorrected CT images 612.

Using the reduced dose data 608, correction terms were generated 616. These correction terms were used to correct the uncorrected sinograms 610 to generate corrected sinograms 618. Like with the uncorrected data sets, the corrected sinograms 618 were reconstructed into corrected CT images 620 and averaged into an ensemble image 622.

To visually analyze the difference between images with and without bias correction, the reference image 606 was subtracted from the uncorrected ensemble image 614 to generate a CT bias image without correction 624. Also, the reference image 606 was subtracted from the corrected ensemble image 622 to generate a CT bias image with correction 626. As can be clearly seen in FIG. 6, the CT bias image without correction 624 shows the phantom, whereas the CT bias image with correction 626 removes the phantom entirely, meaning that the corrected ensemble image 622 is nearly identical to the reference CT image 606.

More particularly, statistical biases in the reduced-dose sinogram 610 were quantified using the Bland-Altman (BA) analysis method. First, a total of 1000 pixel locations within the shadow of the central region of the image object were randomly chosen, where each pixel location corresponded to one point on a BA plot. The horizontal coordinate of the point was given by (y+p)/2, while the vertical coordinate was given by y−p. The 95% limits of agreement (LoA) were calculated using the average difference ±1.96 standard deviation of the difference (across the 1000 data points). Next, both the raw detector count and y were fed to equation (15) to get the bias-corrected sinogram, $\tilde{y}$, 618 and the BA analysis was repeated to study the level of residual bias in $\tilde{y}$.

As described, the standard filtered backprojection (FBP) algorithm was used to reconstruct PCD-CT images from the uncorrected sinogram (y) 612 and the corrected sinogram ($\tilde{y}$) 618. The convolution kernel used in the FBP reconstruction was an apodized ramp kernel that is similar to the Soft reconstruction algorithm used in GE MDCT systems. The reconstruction field-of-view (FOV) is 22 cm and the reconstruction image matrix size is 512×512. The reconstruction slice thickness is 2.8 mm.

Figure 6:
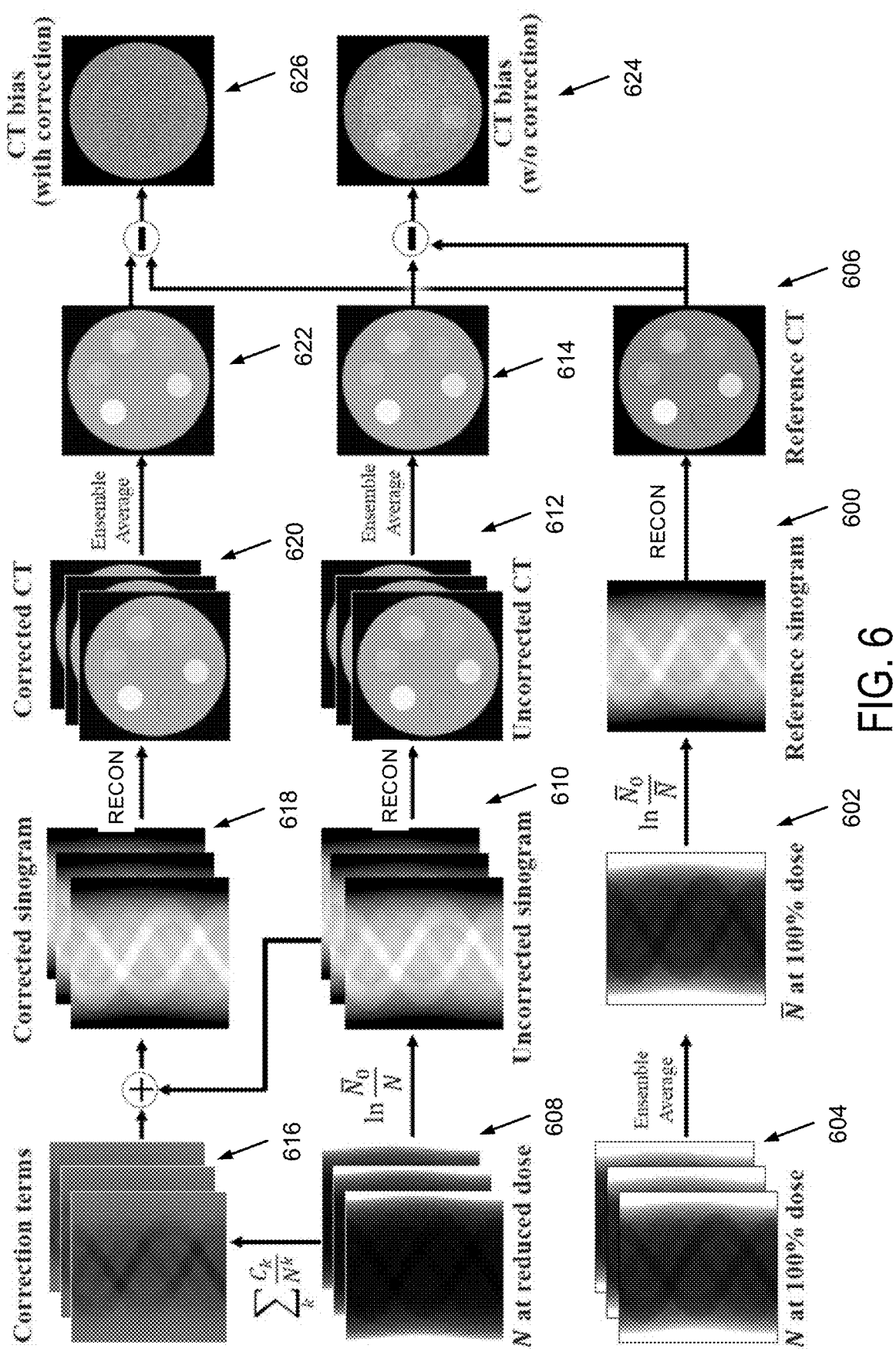
FIG. 6 is schematic illustration of a process for demonstrating the creation of CT images with bias correction.

As shown in FIG. 6, CT number biases at each reduced dose level were measured by subtracting the reduced-dose CT images with the reference CT image. Next, circular regions-of-interests (ROIs), 40 mm² each, were placed on the difference image at locations corresponding to the material inserts in each phantom. The ROI mean±ROI standard deviation gave the average ±standard deviation for the HU bias for a given material at a given dose level. Measurements were performed for both uncorrected and bias-corrected CT images.

To investigate how statistical biases in the energy-bin images and the proposed bias correction method impact the material quantification accuracy in DECT imaging, two-material decomposition was applied to low-energy (LE) bin and high-energy (HE) bin PCD-CT images of the DECT phantom to generate water and iodine basis images for each dose level. The decomposition was performed in the CT image domain using the classical matrix-inversion based method: the matrix elements were experimentally determined by scanning three rods of know materials (water and 15 mg/ml iodine). The water and iodine basis images of each reduced dose level were compared with those generated from the 100% dose gold-standard LE and HE CT images to quantify the statistical biases in the material basis images.

Figure 7:
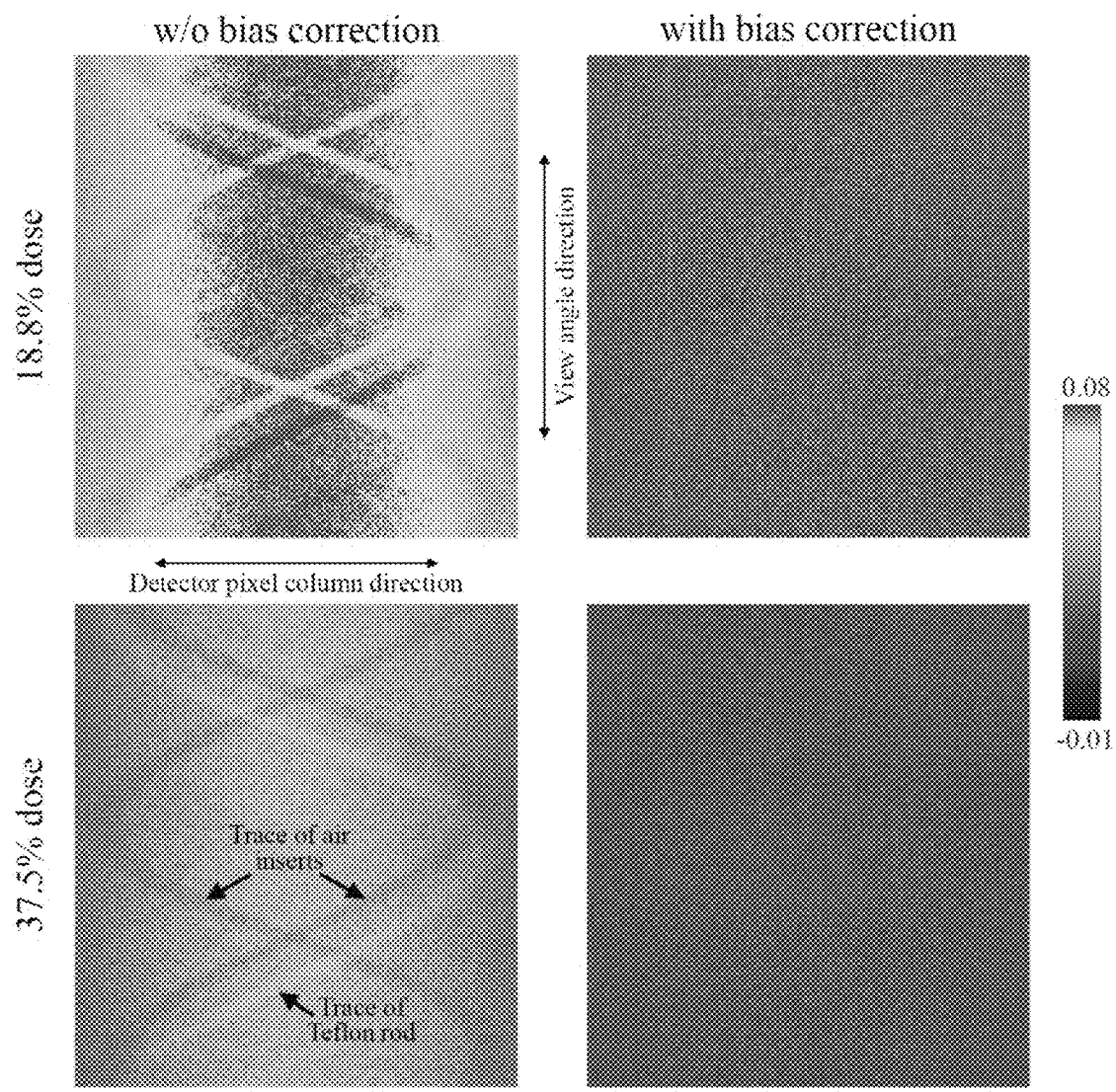
FIG. 7 is a set of colorized sonograms generated by subtracting the sonograms at a given reduced dose level with reference to a standard sinogram.

FIG. 7 shows differences between reduced-dose sinogram and the reference-standard sinogram of the Catphan600 phantom. Without the correction provided by the present disclosure, there are positive statistical biases in the reduced-dose sinogram. In addition, the magnitudes of the sinogram biases depend on the object attenuation, namely p: as shown in FIG. 7, the highest biases are observed at ray locations corresponding to either the center of the phantom or the Teflon rod with the highest attenuation. The magnitudes of the sinogram biases also increase with lower radiation dose level. All of these experimental observations are consistent with the sinogram bias model in equation (7).

Figure 8:
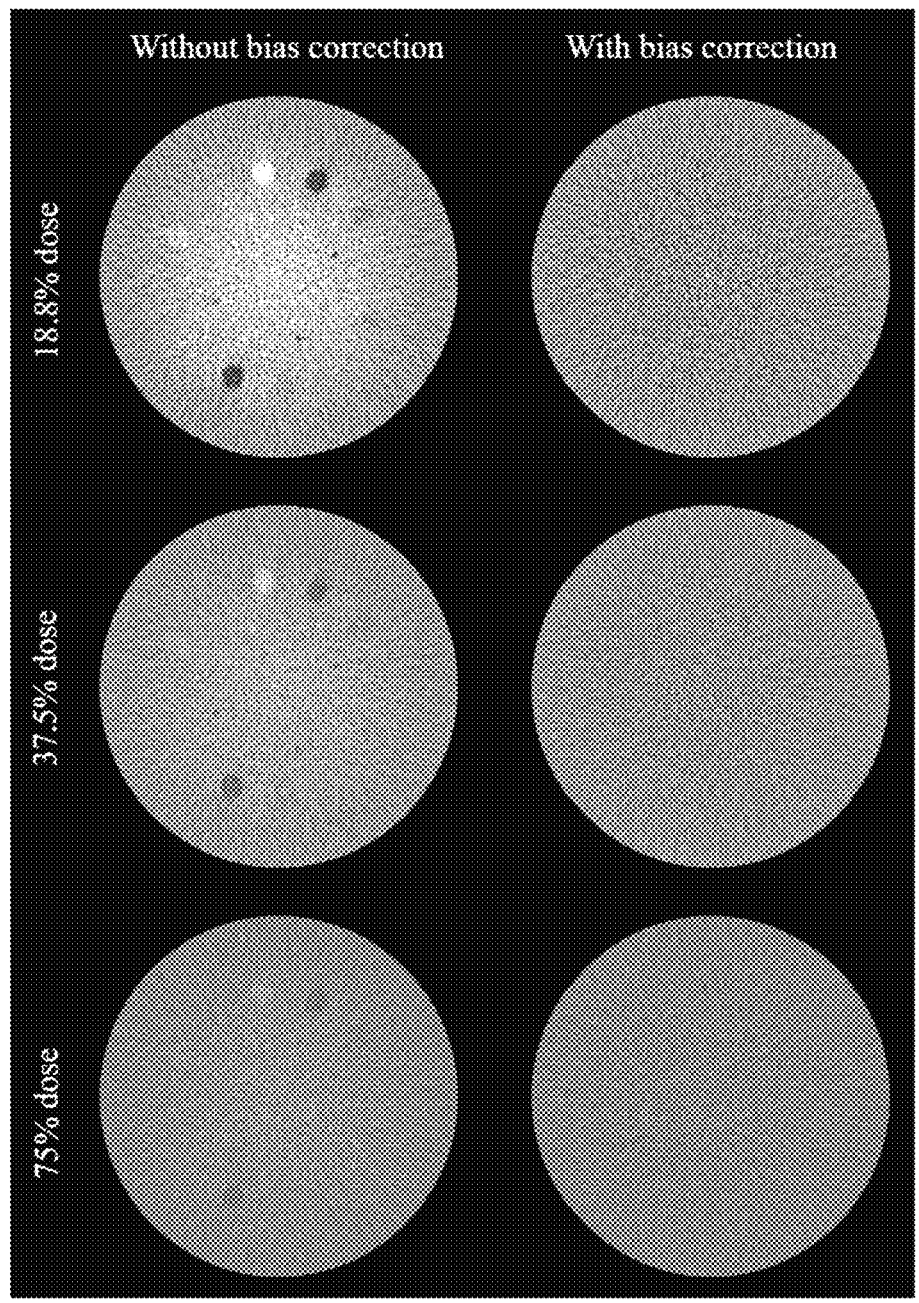
FIG. 8 is a set of correlated images of a phantom generated by subtracting PCCT total energy bin image acquired at each dose level with the reference standard image.

For PCD-CT images of the Catphan600 phantom acquired at reduced dose levels, the difference images relative to the reference-standard image are shown in FIG. 8. Without the bias correction, the difference images clearly demonstrate the existence of CT number bias. The bias is more pronounced at lower radiation dose levels; the polarity of the bias depends on the polarity of the CT number. For example, the positive-HU Teflon rod has a positive bias while the native-HU air insert has a negative bias at reduced dose levels.

Also, FIG. 8 shows that the proposed correction method effectively reduced statistical bias in the CT images: except stochastic image noise, the difference images shown on the right column of FIG. 8 do not show any noticeable features of any material inserts.

Figure 9:
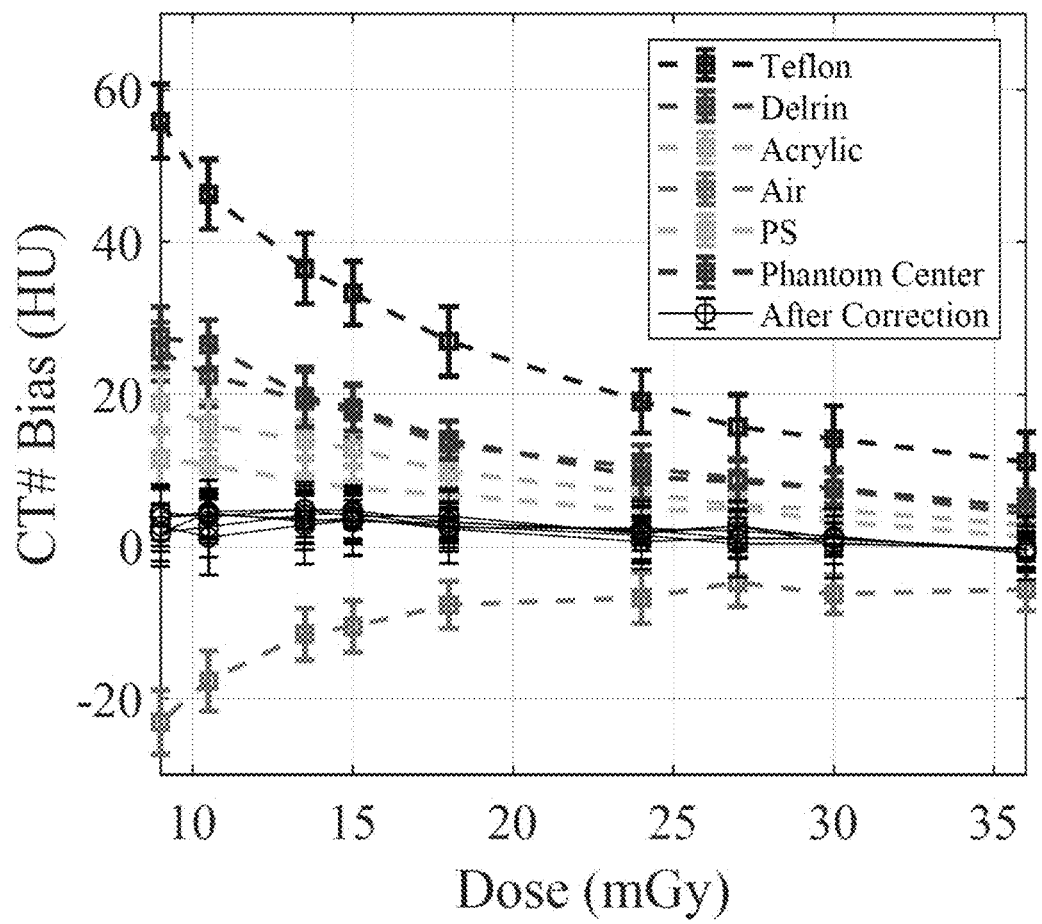
FIG. 9 is a graph showing measured bias values for different inserts in a phantom with and without the proposed bias correction.

Results of quantitative bias measurements are plotted in FIG. 9 as a function of radiation dose level. These quantitative results confirm that without the bias correction, CT number biases increase with lower radiation dose level and higher contrast level; for a given material insert, the polarity of CT number bias is the same as the polarity of the insert's HU. After applying the proposed bias correction scheme, the CT number biases were reduced to be within 5 HU for all inserts at all reduced dose levels. In addition, the post-correction residual biases have negligible dependence on the inserts' material or contrast level. As a result, when a HU contrast is measured for a given feature of interest, the result is no longer biased compared with the value obtained from the 100% dose reference standard image.

Figure 10:
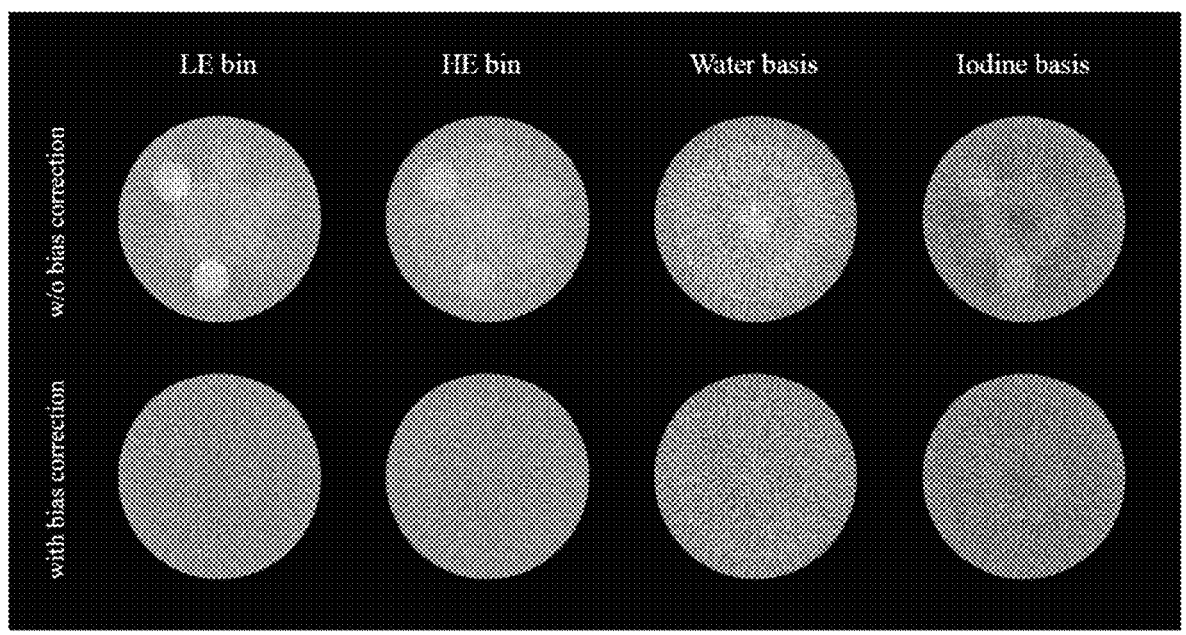
FIG. 10 is a set of correlated images of a DECT characterization phantom generated by subtracting the spectral PCCT images acquired at the 50% dose level with the corresponding reference-standard image shown in FIG. 9.

FIG. 10 shows energy bin images and material basis images of the DECT characterization phantom at the 50% dose level. Without the correction provided by the present disclosure, both the LE and HE bin images demonstrated positive HU biases. Among the 6 inserts, two inserts with the highest contrasts (20 mg/ml iodine and 200 mg/ml calcium) showed the strongest biases. After the material decomposition process, the HU biases were propagated to the water and iodine basis images. For each material insert, the magnitude of its bias image is correlated to the expected signal level in a material image. For example, the 20 mg/ml iodine insert with the highest signal in the iodine basis image also shows the highest bias in that image.

The correction scheme provided herein reduces HU biases in the LE and HE bin images, which effectively improve the water and iodine quantification accuracy. This is demonstrated by both the difference images shown in the second row in FIG. 10.

As described above and shown in the experimental results, reduction of radiation dose levels in CT leads to statistical biases in both the sinogram projection data and the reconstructed CT images. In the sinogram domain, statistical biases in the practically-used projection data $$y_i : \ln \frac{\bar{N}_{i0}}{N_i}$$

are present as positive quantities as shown in equation (7). In other words, the currently-used estimator of the projection data overestimates the desired form of projection data Pi for image reconstruction. Due to the fact that the statistical biases in the sinogram projection data are a sum of terms that are inversely proportional to the power of radiation dose levels, lower radiation dose leads to higher biases in the sinogram data. Furthermore, the magnitudes of the statistical biases in the sinogram projection data domain varies from one data point to another, which prevented the development of robust empirical correction schemes. After the CT reconstruction is performed, the statistical biases naturally migrate from the sinogram domain to the reconstructed CT image domain to manifest themselves as CT number biases.

It is interesting to note that, in stark contrast to the positive biases in the sinogram domain, CT number biases can be either positive or negative and the sign of CT number biases is determined by the relative contrast of a local image feature to its surrounding "background" material. For example, an air cavity inside an object generates a negative CT number bias while a high contrast bony structure generates a positive CT number bias.

Importantly, systems and methods presented herein address the CT number bias issue by constructing an unbiased sinogram data estimator. As a result, the success of the method does not depend on the image reconstruction methods or local image contrast and the techniques is shown to be largely independent of radiation dose level as shown in results. The technique processes each ray in the sinogram domain independently from other rays, which not only guarantees the preservation of spatial resolution but allows each ray to be processed individually (i.e. in parallel fashion). The non-iterative nature of this analytical correction technique further helps reduce the processing time and facilitates its future implementation in clinical systems. As shown above, the technique effectively eradicates statistical biases in both sinogram and CT images. After the correction, the residual CT number bias is less than 5 HU which satisfies the CT number accuracy recommendations of the American College or Radiology CT Quality Control Program. Moreover, the residual biases in the post-correction sinogram and CT images no longer depend on the local contrast level. Instead, they are globally small and positive offsets over the entire domain which are much easier to deal with.

It is worth emphasizing that the systems and methods provided herein address the statistical bias instead of deterministic artifacts in sinogram data processing or reconstruction, although these deterministic artifacts indeed lead to inaccurate CT numbers. For example, it is well known that beam hardening artifacts, scatter artifacts, cone-beam artifacts, truncation artifacts, and other CT artifacts can lead to CT number inaccuracies. However, the severity of the inaccuracies caused by these deterministic artifacts generally do not vary with dose levels. Corrections of these deterministic artifacts are usually under the assumption that the CT number inaccuracies are independent of photon statistics. As shown in the left column of FIG. 9, the statistical biases discussed in this work can lead to a "capping" as opposed to "cupping" caused by beam hardening or scattering. Additionally, the severity of the capping strongly depends on the dose level. This can confound the correction of image artifacts under low dose conditions. Although the systems and methods provided herein are not specifically designed to deal with artifact-induced CT number inaccuracies, it decouples and removes statistical biases from other sources of CT number inaccuracies, allowing artifacts to be better isolated and addressed.

Although the root cause and the correction method of CT number bias are presented in the context of PCD-CT in the non-limiting examples provided herein, the general framework for bias correction can be extended to CT systems with energy-integrating detectors (EIDs). For example, the moments of the distribution of $N_i$ can be calculated based on the actual probability mass function of the EID outputs, leading to new sets of bias correction coefficients ({$C_k$}) for EID-based CT systems. Alternatively, those correction coefficients can be experimentally determined by measuring $y_i$ at different $N_i$ levels.

The fundamental CT imaging equation formulated in equation (3) requires knowledge of the expected photon number at each detector pixel. This requirement is incompatible with the clinical image acquisition process, in which only a single and stochastic sample of the photon number is recorded and used for reconstruction. This violates the fundamental CT imaging equation and generates statistical biases in the CT numbers, particularly at reduced dose levels. The systems and methods provided herein present an analytical correction method that effectively reduces CT number bias without requiring any knowledge of the expected photon number, enabling low-dose CT images to match the quantification accuracy as standard-dose images.

Therefore, a detailed recognition of the root cause of CT number inaccuracy, particularly, at low dose, is provided. An effective correction method is provided to address this long-standing issue in CT imaging. This correction scheme and its experimental validation are presented in the context of PCD-CT which is one of the most important technologies for routinely achieving sub-millisievert CT scanning. While the reduced noise and improved tissue contrast by photon counting detectors can be exploited to decrease patient radiation dose, the severe CT number inaccuracies at reduced dose levels must be addressed before low-dose PCD-CT can be reliably employed in the clinical practice. Additionally, for spectral imaging applications of PCD-CT such as material decomposition and dual K-edge contrast imaging, quantification accuracy depends on an unbiased CT number measurement in each energy bin. As demonstrated by the experimental results, the correction method provided herein not only addresses the CT number bias problem but also improves the material quantification accuracy in spectral PCD-CT images.

As used herein, the phrase "at least one of A, B, and C" means at least one of A, at least one of B, and/or at least one of C, or any one of A, B, or C or combination of A, B, or C. A, B, and C are elements of a list, and A, B, and C may be anything contained in the Specification.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for creating computed tomography (CT) images comprising:
   acquiring or accessing sinogram data;
   determining a photon count for the sinogram data;
   generating unbiased sinogram data from the sinogram data using an unbiased estimator and the photon count; and
   reconstructing a CT image from the unbiased sinogram data.

2. The method of claim 1, wherein determining the photon count includes determining an actual photon count at each of a plurality of detector elements across a field of view.

3. The method of claim 1, wherein determining the photon count includes determining a photon count at all non-zero count detector elements.

4. The method of claim 1, further comprising correcting for detector elements indicating a zero photon count.

5. The method of claim 4, wherein correcting for detector elements indicating a zero photon count includes creating a respective macro-pixel for each detector element indicating a zero photon count and calculating a corrected sinogram for the macro-pixel.

6. The method of claim 1, wherein generating the unbiased sinogram includes selecting coefficients to cancel out statistical biases of terms in a mathematical expansion relating the sinogram data to the photon count.

7. The method of claim 1, further comprising generating the unbiased sinogram data using at least one of:

$$\tilde{y}_i = y_i - \frac{1}{2N_i} + \frac{1}{12N_i^2}$$

$$\tilde{y}_i = y_i - \frac{1}{2N_i} + \frac{1}{12N_i^2} - \frac{1}{120N_i^4}; \text{ or}$$

$$\tilde{y}_i = y_i - \frac{1}{2N_i} + \frac{1}{12N_i^2} + \frac{0}{N_i^3} - \frac{1}{120N_i^4} + \frac{0}{N_i^5} + \frac{1}{252N_i^6};$$

wherein $\tilde{y}_i$, is the unbiased sinogram data, $y_i$, is the sinogram data, and $N_i$ is the photon count.

8. A medical imaging system comprising:
   an x-ray source configured to deliver x-rays to an object as the x-ray source is rotated about the object;
   a detector having a plurality of detector elements configured to receive the x-rays and generate sinogram data therefrom;
   a controller configured to control the x-ray source to deliver the x-rays and to receive the sinogram data from the detector;
   a processor configured to:
      determine a photon count for the sinogram data for a plurality of detector elements;
      generate unbiased sinogram data from the sinogram data using an unbiased estimator and the photon count; and
      reconstruct a CT image from the unbiased sinogram data.

9. The system of claim 8, wherein the processor is further configured to determine the photon count as an actual photon count at each of the plurality of detector elements.

10. The system of claim 8, wherein the processor is further configured to determine the photon count by determining a photon count at all detector elements without a zero photon count.

11. The system of claim 8, wherein the processor is further configured to correct for detector elements indicating a zero photon count.

12. The system of claim 11, wherein the processor is further configured to correct for detector elements indicating a zero photon count by creating a respective macro-pixel for each detector element indicating a zero photon count and calculating a corrected sinogram for the macro-pixel.

13. The system of claim 8, wherein the processor is further configured to generate the unbiased sinogram by selecting coefficients to cancel out statistical biases of terms in a mathematical expansion relating the sinogram data to the photon count.

14. The system of claim 8, wherein the processor is further configured to generate the unbiased sinogram data using at least one of:

$$\tilde{y}_i = y_i - \frac{1}{2N_i} + \frac{1}{12N_i^2};$$

-continued $$\tilde{y}_i = y_i - \frac{1}{2N_i} + \frac{1}{12N_i^2} - \frac{1}{120N_i^4}; \text{ or}$$

$$\tilde{y}_i = y_i - \frac{1}{2N_i} + \frac{1}{12N_i^2} + \frac{0}{N_i^3} - \frac{1}{120N_i^4} + \frac{0}{N_i^5} + \frac{1}{252N_i^6};$$

wherein $\tilde{y}_i$ is the unbiased sinogram data, $y_i$ is the sinogram data, and $N_i$ is the photon count for the plurality of detector elements.

15. A method comprising:
controlling a computed tomography system to acquire biased sinogram data ($y_i$);
determining a photon count ($N_i$) from the sinogram data;
generating unbiased sinogram data ($\tilde{y}_i$) using at least one of:

$$\tilde{y}_i = y_i - \frac{1}{2N_i} + \frac{1}{12N_i^2};$$

$$\tilde{y}_i = y_i - \frac{1}{2N_i} + \frac{1}{12N_i^2} - \frac{1}{120N_i^4}; \text{ or}$$

$$\tilde{y}_i = y_i - \frac{1}{2N_i} + \frac{1}{12N_i^2} + \frac{0}{N_i^3} - \frac{1}{120N_i^4} + \frac{0}{N_i^5} + \frac{1}{252N_i^6};$$

wherein $y_i$ is the sinogram data, and $N_i$ is the photon count for the plurality of detector elements; and
reconstructing an image from the unbiased sinogram data.

16. The method of claim 15, wherein determining the photon count includes determining a photon count for each element of the detector used to acquire the sinogram data having a non-zero count.

17. The method of claim 15, further comprising correcting for each element indicating a zero photon count.

18. The method of claim 17, wherein correcting for each detector element indicating a zero photon count includes creating a respective macro-pixel for each detector element indicating the zero photon count and calculating a corrected sinogram for the macro-pixel.

* * * * *

UNITED STATES PATENT AND TRADEMARK OFFICE
CERTIFICATE OF CORRECTION

PATENT NO. : 12,076,173 B2
APPLICATION NO. : 17/512236
DATED : September 3, 2024
INVENTOR(S) : Guang-Hong Chen et al.

It is certified that error appears in the above-identified patent and that said Letters Patent is hereby corrected as shown below:

In the Specification

Column 8, Line 66, "(•), E(•), and {(•)}" should be --$(\bar{g})$, $E(g)$, and $\langle g \rangle$--.

Column 9, Line 17, "1 represents" should be --$l$ represents--.

Column 9, Line 54, "pi" should be --$p_i$--.

Column 10, Line 16, "parameters at s=0" should be --parameter s at s=0--.

Signed and Sealed this
Fifteenth Day of October, 2024

Katherine Kelly Vidal
*Director of the United States Patent and Trademark Office*